United States Patent
Park et al.

(10) Patent No.: US 7,271,277 B2
(45) Date of Patent: Sep. 18, 2007

(54) FULVENE, METALLOCENE CATALYSTS AND PREPARATION METHOD THEREOF, AND PREPARATION OF POLYOLEFINES COPOLYMER USING THE SAME

(75) Inventors: Young-Whan Park, Daejeon (KR); Si-Geun Lee, Daejeon (KR); Sung-Don Hong, Daejeon (KR); Kwang-Ho Song, Daejeon (KR); Boong-Goon Jeong, Daejeon (KR); Dae-Woo Nam, Daejeon (KR); Bun-Yeol Lee, Daejeon (KR); Choong-Hoon Lee, Daejeon (KR); Hyo-Sun Lee, Daejeon (KR)

(73) Assignee: LG Chem, Ltd. (KR)

( * ) Notice: Subject to any disclaimer, the term of this patent is extended or adjusted under 35 U.S.C. 154(b) by 339 days.

(21) Appl. No.: 10/494,213

(22) PCT Filed: Aug. 29, 2003

(86) PCT No.: PCT/KR03/01763

§ 371 (c)(1),
(2), (4) Date: Apr. 29, 2004

(87) PCT Pub. No.: WO2004/020481

PCT Pub. Date: Mar. 11, 2004

(65) Prior Publication Data
US 2005/0004385 A1    Jan. 6, 2005

(30) Foreign Application Priority Data
Aug. 29, 2002 (KR) .................. 10-2002-0051425
Aug. 29, 2002 (KR) .................. 10-2002-0051426

(51) Int. Cl.
C07F 17/00 (2006.01)
B01J 31/00 (2006.01)
C08F 4/44 (2006.01)
C07C 13/00 (2006.01)

(52) U.S. Cl. .................... 556/52; 556/52; 585/23; 568/379; 526/160; 526/943; 502/103; 502/117

(58) Field of Classification Search .................. 585/23; 556/52, 53; 568/379; 526/160, 943; 502/103, 502/117

See application file for complete search history.

(56) References Cited

U.S. PATENT DOCUMENTS 5,087,677 A    2/1992    Brekner et al. ............. 526/160

(Continued)

FOREIGN PATENT DOCUMENTS

EP    0 577 581 A2    1/1994

(Continued)

OTHER PUBLICATIONS

Lee et al., Organometallics, vol. 21, pp. 1500-1503 (published on the Web Mar. 3, 2002).*

(Continued)

*Primary Examiner*—Porfirio Nazario-Gonzalez
(74) *Attorney, Agent, or Firm*—Cantor Colburn LLP

(57) ABSTRACT

The present invention relates to a novel fulvene compound and a preparation method thereof, and more particularly to a fulvene compound having substituted groups in the 2- and 5-positions, prepared from an unsaturated ketone having a substituted group in the β-position and a halogen atom in the α-position, and a preparation method thereof. The present invention also relates to a metallocene catalyst having a substituted group in the α-position carbon of the bridge of the cyclopentadienyl group only by reaction of a fulvene compound and an anion group including the cyclopentadienyl group, and a preparation method of a polyolefin copolymer using the same.

16 Claims, 3 Drawing Sheets

U.S. PATENT DOCUMENTS

| | | | | |
|---|---|---|---|---|
| 5,470,811 | A | 11/1995 | Jejelowo et al. | 502/117 |
| 5,580,939 | A | 12/1996 | Ewen et al. | 526/127 |
| 5,631,202 | A * | 5/1997 | Ewen | 502/117 |
| 5,688,735 | A | 11/1997 | Ewen et al. | 502/117 |
| 6,166,154 | A | 12/2000 | Oskam et al. | 526/160 |
| 6,258,744 | B1 * | 7/2001 | Beckhaus et al. | 502/118 |
| 6,277,778 | B1 | 8/2001 | Leino et al. | 502/117 |
| 6,403,735 | B1 | 6/2002 | Becke et al. | 526/160 |
| 6,410,661 | B1 * | 6/2002 | Kaminsky et al. | 526/127 |
| 2002/0039963 | A1 | 4/2002 | Takemori et al. | 502/155 |
| 2005/0288461 | A1 * | 12/2005 | Jensen et al. | 526/127 |
| 2005/0288462 | A1 * | 12/2005 | Jensen et al. | 526/127 |

FOREIGN PATENT DOCUMENTS

| | | |
|---|---|---|
| EP | 1 205 497 A2 | 5/2002 |
| WO | WO92/12112 | 7/1992 |
| WO | WO97/28170 | 8/1997 |
| WO | WO99/06448 | 2/1999 |
| WO | WO99/24445 | 5/1999 |

OTHER PUBLICATIONS

"Studies directed toward the synthesis of FS-2: observations on the fragmentation of cyclobutycarbinyl radicals"; Autors: Frederick E. Ziegler, Ranata X. Kover and Nathan N.K. Yee; Tetrahedron Letters, 41, 5155-5159; 2000; pp. 1-5.

Abstract for Canadian Journal of Chemistry (1990), 68(4), 620-7; "Stereoselective synthesis of (2)-boschnialactone (±)-7-epiteucriumlactone and (±)-7-epiisoiridomyrmecine. Study of the Stereochemistry with NMR spectroscopy."; Authors: B. Hanquet, et al.

Abstract for Chemical & Pharmaceutical Bulletin (1995), (43)1, 26-31; "Syntheses of several cyclopentano-monoterpene lactones using 1, 3-dioxin vinylogous ester."; Authors: Masashi Ohba, et al.

Abstract for Synthetic Communications (1985), (15)8, 669-74; "An expedient and stereoselective synthesis of eboschnialactone."; Authors: J.C. Caille, et al.

Won, Y.C., et al., "Fulvene Having Substituents Only on 1-, 4-, and 6-positions: A Key Intermediate for Novel Ansa-metallocene Complexes," Journal of Organometallic Chemistry, vol. 677, pp. 133-139 (2003).

Lee, B.Y., et al., "[2,2'-Methylenebis(1,3-dimethylcyclopentadienyl)]zirconium Dichloride and Its Reactivity in Ethylene-Norbornene Copolymerization," Organometallics, vol. 21, pp. 1500-1503. (2002).

European Search Report, Application No. EP 03 79 1471, Date of Completion: May 22, 2006.

PCT International Search Report International Application No. PCT/KR03/01763; International Filing Date Aug. 29, 2003; Date of Mailing: Dec. 17, 2003.

Brintzinger, et al.; "Stereospecific Olefin Polymerization with Chiral Metallocene Catalysts"; Angew. Chem. Int. Ed. Engl.; vol. 34, pp. 1143-1170; 1995.

Stone, et al.; "An Exceptionally Simple and Efficient Method for the Preparation of a Wide Variety of Fulvenes"; Journal of Organic Chemistry; vol. 49, No. 11; pp. 1849-1853; 1984.

Hua, et al.; "Enantioselective Total Synthesis of (+)-12, 13-Epoxytrichothec-9-ene and Its Antipode"; J. Amer. Chem. Soc.; vol. 110; pp. 4741-4748; 1988.

Bergmann; "Fulvenes and Substituted Fulvenes"; Chemical Review; vol. 68; pp. 41-84; 1968.

* cited by examiner

FULVENE, METALLOCENE CATALYSTS AND PREPARATION METHOD THEREOF, AND PREPARATION OF POLYOLEFINES COPOLYMER USING THE SAME

BACKGROUND OF THE INVENTION (a) Field of the Invention

The present invention relates to a novel fulvene compound and a preparation method thereof, and more particularly to a fulvene compound having substituted groups in the 2- and 5-positions prepared from an unsaturated ketone having a substituted group in the β-position and a halogen atom in the α-position, and a preparation method thereof. The present invention also relates to a metallocene catalyst having a substituted group in the α-position carbon of the bridge of the cyclopentadienyl group made only by reaction of a fulvene compound and an anion group including the cyclopentadienyl group, and a preparation method of a olefin copolymer using the same.

(b) Description of the Related Art

The fulvene compound is a very important intermediate for synthesizing natural product s or transition metal catalysts having cyclopentadienyl groups. A variety of information is given in *Chemical Review*, 1968, 68, 41 regarding the synthesis and reaction of fulvenes.

In general, fulvene is prepared by the reaction of a cyclopentadiene anion and a ketone or an aldehyde. The cyclopentadiene anion may be reacted with an electrophilic carbonyl compound, or cyclopentadiene may be reacted with an electrophile in the presence of a base such as sodium ethoxide.

Also, the Wittig reaction can be used. However, the most recent preparation method is to obtain a fulvene derivative by reacting a cyclopentadiene derivative with an electrophile in the presence of pyrrolidine (*Journal of Organic Chemistry* 1984, 49, 1849).

The fulvene compound can be purified by column chromatography for a smaller scale, and by distillation or recrystallization for a larger scale.

Generally, a fulvene compound is prepared by the following Schemes 1 and 2:

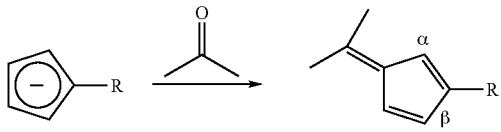

Scheme 1

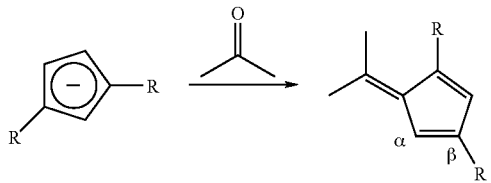

Scheme 2

In Schemes 1 and 2, the fulvene derivative may or may not have substituents on the pentagonal ring. In the conventional method, it is impossible to add substituted groups at the 2- and 5-positions of the pentagonal ring simultaneously, because a cyclopentadienyl anion or cyclopentadiene having a substituent is reacted with a ketone or an aldehyde. That is, in Scheme 1, the substituent is mainly added to the β-position instead of α-position of the cyclopentadiene due to steric hindrance. Also, in Scheme 2, when a cyclopentadienyl anion having two substituents in the 1- and 3-positions is reacted with an electrophile, a fulvene having substituents at the α- and β-positions is produced exclusively, but one having substituents at both α-positions is not produced.

A group 4 transition metal compound having one or two cyclopentadienyl group(s) as a ligand may be activated with methylaluminoxane or a boron compound to be used as an olefin polymerization catalyst (U.S. Pat. No. 5,580,939). This catalyst shows unique characteristics that cannot be offered by the conventional Ziegler-Natta catalyst. That is, it has a narrow molecular weight distribution, offers good reactivity to secondary monomers such as α-olefins or cyclic olefins, and the prepared copolymers have a uniform secondary monomer distribution. Moreover, stereoselectivity can be controlled by changing the substituent of the cyclopentadienyl ligand during α-olefin polymerization (*Angew. Chem. Int. Ed. Engl.* 1995, 34, 1143), and the degree of copolymerization, molecular weight, secondary monomer distribution, etc. can be controlled during copolymerization of ethylene and other olefins (U.S. Pat. No. 5,470,811).

With the development of catalyst systems, efforts to find catalysts suitable for copolymerization of ethylene and an α-olefin (LLDPE, VLDPE, EPM, and EPDM), for copolymerization of ethylene and a cyclic olefin, for copolymerization of an α-olefin and a cyclic olefin [cyclic olefin copolymer (COC)], and for copolymerization of ethylene, α-olefin, and styrene, are continuously being made. Such copolymerization requires catalysts with good activity, superior reactivity for the secondary monomer, and uniform secondary monomer distribution.

Other than the Ziegler-Natta catalyst, metallocene catalysts are used for such copolymerization. Because the metallocene catalyst is more expensive than the Ziegler-Natta catalyst, it should have good activity to be economically viable. If the metallocene catalyst has good reactivity for the secondary monomer, it is possible to obtain a polymer comprising a lot of secondary monomers with a small amount of catalyst.

As a result of much research on copolymerization using a variety of catalysts, it has been proved that ansa-type metallocene catalyst has good reactivity for the secondary monomer in general. According to F. J. Karol's research, when producing an LLDPE with a density of 0.93 using hexene as a secondary monomer in the presence of a bridged catalyst, an ethylene/hexene ratio of 0.004 to 0.005 is sufficient. However, for a non-bridged catalyst, the ethylene/hexane ratio should be at least 0.02 (1997. 4. 18. US Palm Coast, Fla., Polymer Reaction Engineering Foundation Conference).

Therefore, the catalyst having bridged ligand structure has attracted interest. Also, the catalyst having bridged ligand structure can control the molecular structure of the propylene polymer depending on the molecular symmetry.

The catalysts having bridged ligand structure developed thus far can be classified into three types depending on the bridge type. The first is a catalyst in which two cyclopentadienyl ligands connected by the reaction of indene or fluorene with an electrophile such as an alkyl halide; the second is a silicon bridged catalyst connected by —SiR$_2$—; and the third is a methylene bridged catalyst obtained by the reaction of fulvene and indene or fluorene. The following Schemes 3 to 5 are representative syntheses for these catalysts.

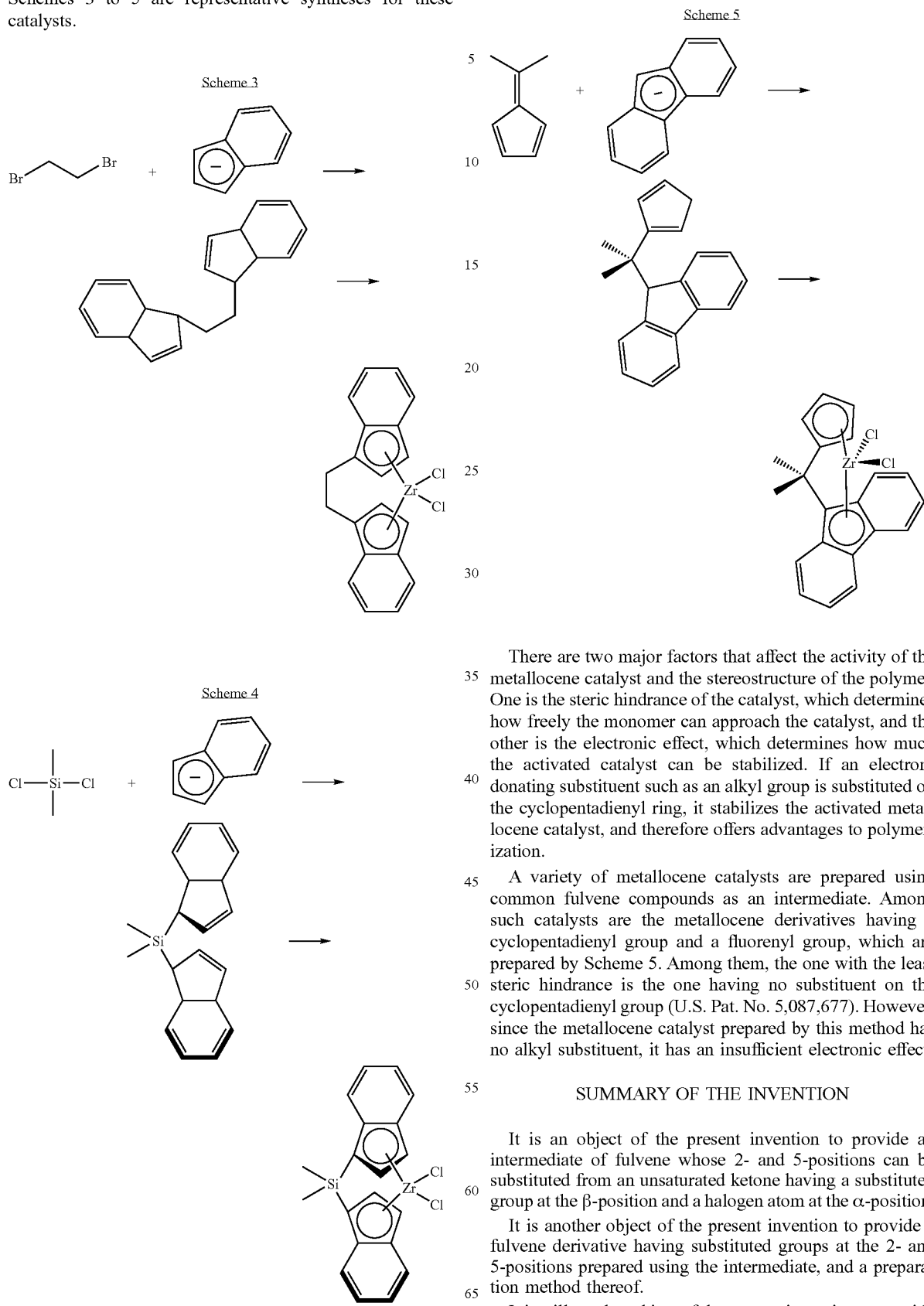

There are two major factors that affect the activity of the metallocene catalyst and the stereostructure of the polymer. One is the steric hindrance of the catalyst, which determines how freely the monomer can approach the catalyst, and the other is the electronic effect, which determines how much the activated catalyst can be stabilized. If an electron-donating substituent such as an alkyl group is substituted on the cyclopentadienyl ring, it stabilizes the activated metallocene catalyst, and therefore offers advantages to polymerization.

A variety of metallocene catalysts are prepared using common fulvene compounds as an intermediate. Among such catalysts are the metallocene derivatives having a cyclopentadienyl group and a fluorenyl group, which are prepared by Scheme 5. Among them, the one with the least steric hindrance is the one having no substituent on the cyclopentadienyl group (U.S. Pat. No. 5,087,677). However, since the metallocene catalyst prepared by this method has no alkyl substituent, it has an insufficient electronic effect.

SUMMARY OF THE INVENTION

It is an object of the present invention to provide an intermediate of fulvene whose 2- and 5-positions can be substituted from an unsaturated ketone having a substituted group at the β-position and a halogen atom at the α-position.

It is another object of the present invention to provide a fulvene derivative having substituted groups at the 2- and 5-positions prepared using the intermediate, and a preparation method thereof.

It is still another object of the present invention to provide a metallocene catalyst having little steric hindrance and superior copolymerization ability and polymerization activity using the fulvene compound, and a preparation method thereof.

It is still another object of the present invention to provide a preparation method of polymer of an α-olefin and a cyclic olefin using the metallocene catalyst.

To attain the objects, the present invention provides an intermediate of a fulvene compound represented by the following Chemical Formula 9:

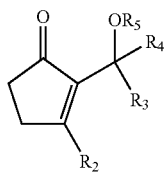

Chemical Formula 9 wherein
each of $R_2$, $R_3$, and $R_4$ is individually or simultaneously a hydrogen; a $C_1$ to $C_{20}$ alkyl, alkenyl, alkylaryl, arylalkyl, or aryl; a $C_1$ to $C_{20}$ alkyl or aryl having an oxygen atom or a nitrogen atom; or a group 14 metalloid radical substituted by a hydrocarbyl, wherein $R_3$ and $R_4$ may be connected to form a ring; and $R_5$ is a $C_1$ to $C_{20}$ alkyl, alkenyl, alkylaryl, arylalkyl, or aryl; a $C_1$ to $C_{20}$ alkyl or aryl having an oxygen atom or a nitrogen atom; or a group 14 metalloid radical substituted by a hydrocarbyl.

The present invention also provides a fulvene compound represented by the following Chemical Formula 7:

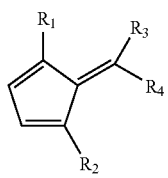

Chemical Formula 7 wherein each of $R_1$, $R_2$ $R_3$, and $R_4$ is individually or simultaneously a hydrogen; a $C_1$ to $C_{20}$ alkyl, alkenyl, alkylaryl, arylalkyl, or aryl; or a group 14 metalloid radical substituted by a hydrocarbyl, and at least one of $R_1$ and $R_2$ is not a hydrogen, and $R_3$ and $R_4$ may be connected by an alkylidine radical including an alkyl or aryl radical to form a ring.

The present invention also provides a preparation method of a fulvene compound represented by Chemical Formula 7, which comprises:

a) a step of lithiating a ketal (dioxolane group) derivative represented by the following Chemical Formula 13, reacting it with an electrophile represented by the following Chemical Formula 12, and then hydrolyzing it to obtain the compound represented by the following Chemical Formula 11;

b) a step of reacting the compound represented by Chemical Formula 11 with a compound represented by the following Chemical Formula 10, or dihydropyran, or isobutene, to obtain the compound represented by the following Chemical Formula 9 by protecting the alcohol group; and c) a step of reacting (nucleophilic reaction) the fulvene intermediate represented by Chemical Formula 9 with an organometallic compound represented by the following Chemical Formula 8a or with an organometallic compound represented by the following Chemical Formula 8b:

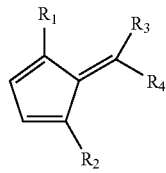

Chemical Formula 7

$R_1$-M    Chemical Formula 8a $R_1$-MgX    Chemical Formula 8b

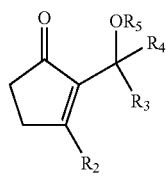

Chemical Formula 9

$R_5$—Y    Chemical Formula 10

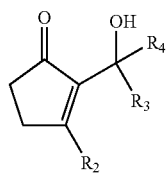

Chemical Formula 11

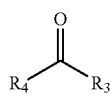

Chemical Formula 12

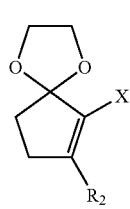

Chemical Formula 13 wherein
each of $R_1$, $R_2$, $R_3$, $R_4$, and $R_5$ is the same as defined above;

X is a halogen atom;

Y is a leaving group of the nucleophilic substitution, which is halogen, trifluoromethylsulfonate, or p-toluenesulfonate; and M is an alkali metal.

The present invention also provides an intermediate for natural product synthesis, a medicine intermediate, or an intermediate of a metallocene catalyst for olefin polymerization prepared from the fulvene compound represented by Chemical Formula 7.

The present invention also provides a compound represented by the following Chemical Formula 5:

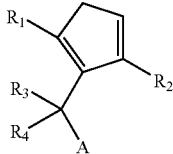

Chemical Formula 5 wherein each of $R_1$, $R_2$, $R_3$, and $R_4$ is the same as defined above; and A is cyclopentadienyl or its derivative, fluorenyl or its derivative, indenyl or its derivative, a substituted or unsubstituted amido, or a substituted or unsubstituted phosphino.

In the compound represented by Chemical Formula 5, if both $R_1$ and $R_2$ are methyl, and $R_3$ and $R_4$ are hydrogen simultaneously or individually or both of them are phenyl, it is preferable that A is fluorenyl or its derivative.

The present invention also provides a metallocene catalyst represented by the following Chemical Formula 1:

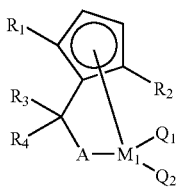

Chemical Formula 1 wherein each of $R_1$, $R_2$, $R_3$, $R_4$, and A is the same as defined above;

$M_1$ is a group 4 transition metal; and each of $Q_1$ and $Q_2$ is individually or simultaneously a halogen; a $C_1$ to $C_{20}$ alkyl, alkenyl, alkylaryl, arylalkyl, or aryl; a $C_1$ to $C_{20}$ substituted or unsubstituted alkylidene; a substituted or unsubstituted amido; or a $C_1$ to $C_{20}$ alkylalkoxy or arylalkoxy.

The present invention also provides a preparation method of the metallocene catalyst represented by Chemical Formula 1, which comprises:

a) a step of reacting a fulvene compound represented by Chemical Formula 7 with a cyclopentadiene derivative to obtain the compound represented by Chemical Formula 5; and b) a step of reacting the compound represented by Chemical Formula 5 with a compound represented by the following Chemical Formula 6:

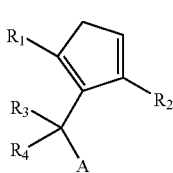

$M_1(Q_1)(Q_2)$

Chemical Formula 5

Chemical Formula 6

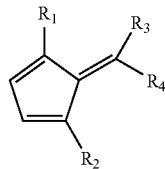

Chemical Formula 7

In Chemical Formula 5, Chemical Formula 6, and Chemical Formula 7, each of $R_1$, $R_2$, $R_3$, $R_4$, $M_1$, A, $Q_1$, and $Q_2$ is the same as defined above.

The present invention also provides a preparation method of an ethylenic polyolefin polymer and copolymer comprising a step of polymerizing one or more kinds of monomers selected from a group consisting of ethylene, an α-olefin, a diene monomer, a triene monomer, and a styrene monomer in the presence of the metallocene catalyst represented by Chemical Formula 1.

The present invention also provides a preparation method of a cyclic olefin copolymer (COC) comprising a step of polymerizing an α-olefin and a cyclic olefin in the presence of the metallocene catalyst represented by Chemical Formula 1.

DETAILED DESCRIPTION OF THE PREFERRED EMBODIMENTS

Figure 1:
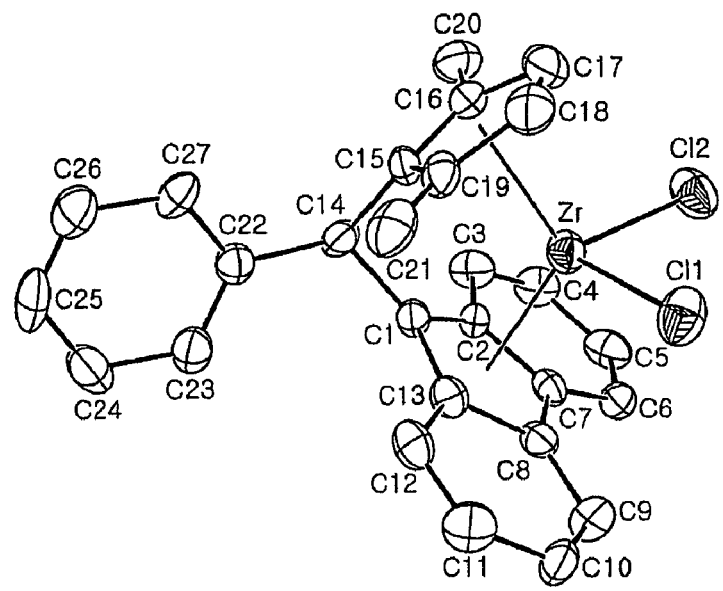
FIG. 1 shows an X-ray diffraction crystal structure of benzylidene(fluorenyl)(1,3-dimethylcyclopentadienyl)zirconium dichloride prepared in Example 5.

Hereinafter, the present invention is described in more detail.

The present invention relates to a novel fulvene compound having substituted groups at the 2- and 5-positions, and a preparation method thereof. The present invention also relates to a metallocene catalyst using the fulvene compound, a preparation method thereof, and a preparation method of a polyolefin copolymer using the same.

Differing from the conventional preparation of fulvene by the reaction of a cyclopentadienyl anion or cyclopentadiene with an electrophile, the present invention is characterized by preparing a fulvene compound from an unsaturated ketone having a substituted group at the β-position and a halogen atom at the α-position. That is, a ketone is substituted by a ketal protecting group and is converted into a lithium salt. It is then reacted with an aldehyde or a ketone to obtain an α,β-unsaturated ketone having a hydroxy group. Then, through a nucleophilic addition reaction, a novel organic fulvene compound having substituted groups at the 2- and 5-positions, which is represented by Chemical Formula 7, is obtained. The fulvene compound prepared by the present invention can be used for an intermediate for natural product synthesis, a medicine intermediate, or an olefin intermediate for olefin polymerization using a metallocene catalyst.

Preferably, in the fulvene compound represented by Chemical Formula 7, $R_1$ and $R_2$ are not hydrogens, and at least one of $R_3$ and $R_4$ is an aryl radical. Also preferably, $R_1$ and $R_2$ are methyl radicals, and both $R_3$ and $R_4$ are phenyls, or one is a phenyl and the other is hydrogen.

The fulvene compound represented by Chemical Formula 7 is prepared by the following Scheme 6:

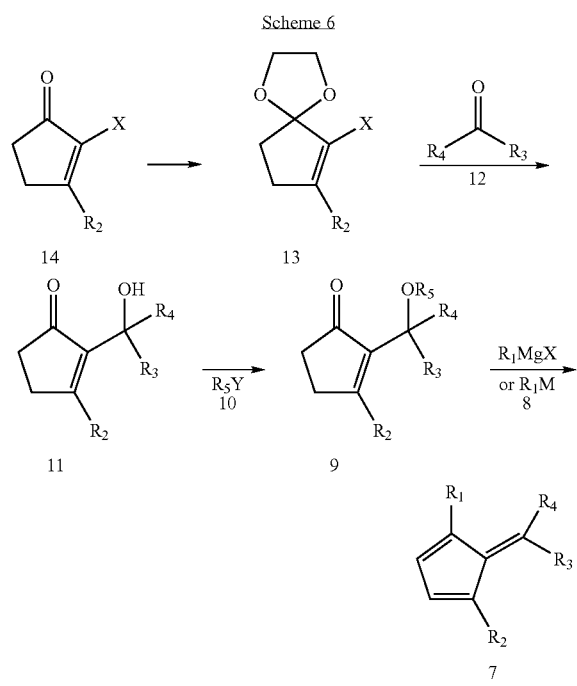

As shown in Scheme 6, a novel intermediate represented by Chemical Formula 9 is prepared from an unsaturated ketone (Chemical Formula 14) having a substituted group $R_2$ at the β-position and a halogen atom at the α-position, in order to prepare a fulvene compound having substituted groups at the 2- and 5-positions, which is represented by Chemical Formula 7.

For this purpose, the carbonyl group of a commercially available unsaturated ketone (Chemical Formula 14) is converted to prepare a ketal (dioxolane group) derivative represented by Chemical Formula 13. In Chemical Formula 14, X is a halogen atom including iodine, bromine, and chlorine. Preferably, X is Br.

Then, the compound represented by Chemical Formula 13 is made into a lithium salt using butyllithium, etc. at a low temperature (preferably −78° C.) and under a dehydrated atmosphere. It is then reacted with an electrophile represented by Chemical Formula 12 to obtain the compound represented by Chemical Formula 11. $R_3$ and $R_4$ are determined by the structure of the electrophile. The ketal group (dioxolane group) protecting the carbonyl is easily deprotected during the purification process, e.g., column chromatography. Or, it is easily hydrolyzed by an acid treatment to give the compound represented by Chemical Formula 11.

Then, the alcohol group of the compound represented by Chemical Formula 11 is protected to prepare the compound represented by Chemical Formula 9. That is, the compound represented by Chemical Formula 11 is reacted with a compound represented by Chemical Formula 10, dihydropyran, or isobutene, which have a double bond, and are used for alcohol group protection, to prepare the compound represented by Chemical Formula 9. In Chemical Formula 10, the protecting group $R_5$ may be diverse. Preferably, dihydropyran which is known as the best protecting group is used, or an anion of the compound represented by Chemical Formula 11 is reacted with alkyl halide. Or, any protecting groups having an ether linkage may be used.

The ketone compound represented by Chemical Formula 9 is reactive to nucleophile and can be converted to a tertiary alcohol under attack by organometallic compound represented by the following Chemical Formula 8a or Chemical Formula 8b. Then, it is dehydrated by acid treatment to obtain a cyclopentadiene having an alcohol protecting group $R_5$.

$R_1$-M       Chemical Formula 8a $R_1$—MgX      Chemical Formula 8b wherein each of $R_1$, X, and M is the same as defined above; and M is preferably Li or Na.

The $R_1$ group of the obtained fulvene compound can be controlled by the organometallic compound used. Preferably, a $C_1$ to $C_{20}$ alkyllithium or aryllithium represented by Chemical Formula 8a is used for the organometallic compound. And more preferably, a Grignard reagent represented by Chemical Formula 8b is used.

Then, the cyclopentadiene is dehydrogenated with a strong base like sodium ethoxide to obtain a cyclopentadienyl anion, so that the protecting group like the tetrahydropyranyl (THP) group is removed. Or, an ether compound is prepared from an alkyl halide and an alcohol, so that the alkoxide anion is removed.

From the fulvene compound having substituted groups at the 2- and 5-positions, which is prepared by the present invention, an intermediate for natural product syntheses, a medicine intermediate, or a metallocene catalyst having a cyclopentadienyl group can be prepared. The metallocene catalyst can be used for olefin polymerization in combination with an aluminum compound or a boron compound.

The present invention also provides a bridged metallocene catalyst having only one carbon atom bridge of two cyclopentadienyl ligands and substituent(s) only at the α-position to the bridgehead carbon, which is prepared from the fulvene derivative having substitutuent(s) at the 2- and/or 5-positions. The present invention also provides a preparation method of an ethylene polymer and a copolymer or a cyclic olefin copolymer using the metallocene catalyst.

The bridged metallocene catalyst having a substituent at the α-position of the cyclopentadienyl group only has many advantages.

Particularly, with regard to preparation of a cyclic olefin copolymer, the part, where monomers are bound and the polymer grows is the opposite side of the bridge, which is close to the β-position of the cyclopentadienyl group. Since the metallocene catalyst of the present invention has substituents only at the α-position, the steric hindrance caused by the substituents is minimized but the catalyst's electronic effect is optimized, thereby the polymerization activity is increased. Therefore, the metallocene catalyst of the present invention, which has no substituent at the β-position, easily accepts a monomer with fairly large steric hindrance, and the copolymerization becomes facile.

In the metallocene compound represented by Chemical Formula 1, A is preferably cyclopentadienyl, indenyl, or fluorenyl, or a derivative thereof substituted by one or more $C_1$ to $C_{20}$ alkyl, alkenyl, alkylaryl, arylalkyl, or aryl. Both $R_1$ and $R_2$ are preferably methyl. Also preferably, in the metallocene catalyst represented by Chemical Formula 1, A is a substituted or unsubstituted amido group, and all of $R_1$, $R_2$, $R_3$, and $R_4$ are $C_1$ to $C_{20}$ alkyls or aryls. In the metallocene compound represented by Chemical Formula 1, it is further preferable that A is a substituted or unsubstituted phosphino group, and all of $R_1$, $R_2$, $R_3$, and $R_4$ are $C_1$ to $C_{20}$ alkyls or aryls.

The metallocene compound of the present invention is prepared by the following Scheme 7:

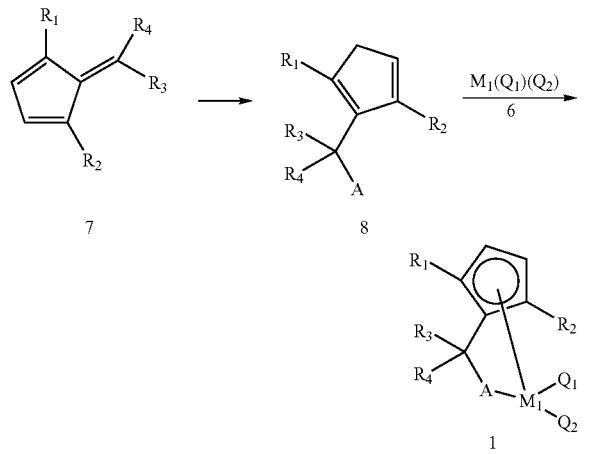

As shown in Scheme 7, the fulvene compound having substituted groups at the 2- and 5-positions (Chemical Formula 7) is reacted with an anion of a cyclopentadiene derivative to obtain the compound represented by Chemical Formula 5. For the cyclopentadiene derivative, cyclopentadienyl or its derivative, indenyl or its derivative, fluorenyl or its derivative, a substituted or unsubstituted amido group, or a substituted or unsubstituted phosphino group may be used.

Then, the compound represented by Chemical Formula 5 is prepared into the metallocene compound represented by Chemical Formula 1 by a variety of methods reported in the literature. Preferably, the compound represented by Chemical Formula 5 may be reacted with the compound represented by Chemical Formula 6.

To take a preferred example, the compound represented by Chemical Formula 5 is treated with 2 equivalents of n-butyllithium to dehydrogenate the cyclopentadiene and the fluorene group to form a cyclopentadienyl anion and a fluorenyl anion, respectively. Then, through a reaction with a metal halide compound, etc., a bridged metallocene compound comprising a cyclopentadienyl group which has only one carbon at the bridge position and a substituent at the α-position only, can be prepared.

The present invention also provides a preparation method of an ethylenic olefin polymer and a copolymer, which comprises a step of polymerizing one or more kinds of monomers selected from a group consisting of ethylene, an α-olefin, a diene monomer, a triene monomer, and a styrene monomer in the presence of the metallocene catalyst represented by Chemical Formula 1.

The present invention also provides a cyclic olefin copolymer (COC) prepared by the polymerization of an α-olefin and a cyclic olefin using the metallocene compound represented by Chemical Formula 1 as a catalyst.

And, one or more compounds selected from a group consisting of a linear, cyclic, or clustered compound represented by the following Chemical Formula 2; a compound represented by the following Chemical Formula 3; and a compound represented by the following Chemical Formula 4a or Chemical Formula 4b can be used as a cocatalyst in cyclic olefin copolymerization:

—[Al($R_6$)—O]$_a$—  Chemical Formula 2 wherein $R_6$ is a halogen, a $C_1$ to $C_{20}$ hydrocarbyl radical, or a $C_1$ to $C_{20}$ hydrocarbyl radical substituted by a halogen, individually or simultaneously; and a is an integer of 2 to 5000;

N($R_6$)$_3$  Chemical Formula 3 wherein

N is a group 13 element; and each of three $R_6$'s is individually or simultaneously a halogen, a $C_1$ to $C_{20}$ hydrocarbyl radical, or a $C_1$ to $C_{20}$ hydrocarbyl radical substituted by a halogen;

[L-H]$^+$[NE$_4$]$^-$  Chemical Formula 4a

[L]$^+$[NE$_4$]$^-$  Chemical Formula 4b wherein

L is a neutral or cationic Lewis acid;

N is a group 13 element; and each of four E's is individually or simultaneously a $C_6$ to $C_{20}$ aryl radical substituted by one or more substituents selected from a group consisting of a halogen, a $C_1$ to $C_{20}$ hydrocarbyl, a $C_1$ to $C_{20}$ alkoxy, and a phenoxy radical.

For the compound represented by Chemical Formula 2, there are methylaluminoxane, ethylaluminoxane, isobutylaluminoxane, butylaluminoxane, and so forth.

For the alkyl metal compound represented by Chemical Formula 3, there are trimethylaluminum, triethylaluminum, triisobutylaluminum, tripropylaluminum, tributylaluminum, dimethylchloroaluminum, triisopropylaluminum, tri-t-butylaluminum, tricyclopentylaluminum, tripentylaluminum, triisopentylaluminum, trihexylaluminum, ethyidimethylaluminum, methyidiethylaluminum, triphenylaluminum, tri-p-tolylaluminum, dimethylaluminum methoxide, dimethylaluminum ethoxide, trimethylboron, triethylboron, triisobutylboron, tripropylboron, tributylboron, tris(pentafluorophenyl)boron, and so forth.

For the compound represented by Chemical Formula 4a or 4b, there are triethylammonium tetraphenylborate, tributylammonium tetraphenylborate, trimethylammonium tetraphenylborate, tripropylammonium tetraphenylborate, trimethylammonium tetra(p-tolyl)borate, trimethylammonium tetra(o,p-dimethylphenyl)borate, tributylammonium tetra(p-trifluoromethylphenyl)borate, trimethylammonium tetra(p-trifluoromethylphenyl)borate, tributylammonium tetra(pentafluorophenyl)borate, N,N-dimethylanilinium tetraphenylborate, N,N-diethylanilinium tetraphenylborate, N,N-dimethylanilinium tetra(pentafluorophenyl)borate, diethylammonium tetra(pentafluorophenyl)borate, triphenylphosphonium tetraphenylborate, trimethylphosphonium tetraphenylborate, triethylammonium tetraphenylaluminate, tributylammonium tetraphenylaluminate, trimethylammonium tetraphenylaluminate, tripropylammonium tetraphenylaluminate, trimethylammonium tetra(p-tolyl)aluminate, tripropylammonium tetra(p-tolyl)aluminate, triethylammonium tetra(o,p-dimethylphenyl )aluminate, tributylammonium tetra(p-trifluoromethylphenyl)aluminate, trimethylammonium tetra(p-trifluoromethylphenyl)aluminate, tributylammonium tetrapentafluorophenylaluminate, N,N-dimethylanilinium tetraphenylaluminate, N,N-diethylanilinium tetraphenylaluminate, N,N-diethylanilinium tetra (pentafluorophenyl)aluminate, diethylammonium tetra (pentafluorophenyl)aluminate, triphenylphosphonium tetraphenylaluminate, trimethylphosphonium tetraphenylaluminate, triethylammonium tetraphenylaluminate, tributylammonium tetraphenylaluminate, trimethylammonium tetraphenylborate, tripropylammonium tetraphenylborate, trimethylammonium tetra(p-tolyl)borate, tripropylammonium tetra(p-tolyl)borate, triethylammonium tetra(o,p-dimethylphenyl)borate, trimethylammonium tetra(o,p-dimethylphenyl)borate, tributylammonium tetra(p-trifluoromethylphenyl)borate, trimethylammonium tetra(p-trifluoromethylphenyl)borate, tributylammonium tetra (pentafluorophenyl)borate, N,N-dimethylanilinium tetraphenylborate, N,N-diethylanilinium tetraphenylborate, N,N-dimethylanilinium tetra(pentafluorophenyl)borate, diethylammonium tetra(pentafluorophenyl)borate, triphenylphosphonium tetraphenylborate, triphenylcarbonium tetra(p-trifluoromethylphenyl)borate, triphenylcarbonium tetra(pentafluorophenyl)borate, and so forth.

The metallocene catalyst represented by Chemical Formula 1 and the cocatalyst represented by Chemical Formulas 2 to 4 may be used while supported on silica or alumina.

For olefin monomers that are polymerizable using the catalyst and the cocatalyst, there are ethylene, α-olefins, cyclic olefins, and so forth. Also, a dienic olefin monomer or a trienic olefin monomer having more than two double bonds can be used in polymerization. For such monomers, there are ethylene, propylene, 1-butene, 1-pentene, 4-methyl-1-pentene, 1-hexene, 1-heptene, 1-decene, 1-undecene, 1-dodecene, 1-tetradecene, 1-hexadecene, 1-icocene, norbornene, norbonadiene, ethylidenenorbornene, phenyl norbornene, vinylnorbornene, dicyclopentadiene, 1,4-butadiene, 1,5-pentadiene, 1,6-hexadiene, styrene, α-methylstyrene, divinylbenzene, 3-chloromethylstyrene, and so forth. More than one kind of these monomers can be used to prepare a copolymer.

The novel fulvene compound of the present invention which has substituted groups at the 2- and 5-positions can be used as an intermediate for natural product synthesis, a medicine intermediate, or a starting material for preparation of a metallocene catalyst having a cyclopentadienyl group.

Also, the bridged metallocene derivative prepared from the fulvene derivative can be used for olefin polymerization, or in combination with an aluminum compound or a boron compound. Since the metallocene catalyst prepared by the present invention has less steric hindrance and offers better electronic effects than the fulvene compound prepared by the conventional method, it is useful for polymerization and copolymerization of large-sized monomers, as for a cyclic olefin copolymer (COC).

Hereinafter, the present invention is described in more detail through examples. However, the following examples are only for the understanding of the present invention, and the present invention is not limited by the following examples.

EXAMPLES

Organic reagents and solvents required for preparation of the fulvene compound and the catalyst were purchased from Aldrich and Merck and purified by the standard method. Contact with air and moisture was prevented in all synthesis steps to increase experimental reproducibility. The structure of compounds was identified with 300 MHz Bruker NMR study.

Example 1

Preparation of ketal-substituted 2-bromo-3-methyl-2-cyclopentene-1-one

From 2-bromo-3-methyl-2-cyclopenten-1-one purchased from Aldrich, ketal-substituted 2-bromo-3-methyl-2-cyclopentene-1-one was prepared according to the method reported in the literature (J. Am. Chem. Soc. 1988,110, 4741)).

Example 2

Preparation of 2-(hydroxy-phenyl-methyl)3-methyl-2-cyclopentene-1-one 0.550 g (2.54 mmol) of the ketal-substituted 2-bromo-3-methyl-2-cyclopentene-1-one prepared in Example 1 was dissolved in 9.0 mL of tetrahydrofuran. Then, 1.02 mL (2.54 mmol) of 2.5M n-butyllithium was added dropwise to the solution at −78° C. The solution was reacted for 1 hour to obtain a lithium salt. 0.270 g (2.54 mmol) of benzaldehyde was slowly added to the reaction mixture, and the solution was reacted for about 1 hour at the same temperature. The reaction mixture was poured into a separatory funnel containing 10 mL of distilled water. Then, the solution was extracted with 30 mL of ethyl acetate. After removing residual moisture with anhydrous magnesium sulfate, the solvent was removed in vacuo. The obtained product, which included impurities, was separated by column chromatography eluted with a 3:1 (v/v) mixture solution of ethyl acetate and n-hexane. The obtained ketal protecting group (dioxolane group) is easily converted to a ketone compound due to the silica gel during the column chromatography. The yield of the obtained compound was 0.440 g (96%).

$^1$H NMR (CDCl$_3$): δ 7.20–7.36 (m, 5H), 5.59 (d, J=9.1 Hz, 1H, OH), 4.58 (d, J=9.1 Hz, 1H, CH—O), 2.60–2.50 (m, 2H), 2.45–2.35(m, 2H), 2.10(s, 3H, CH$_3$). $^{13}$C NMR (CDCl$_3$): δ 210.60 (carbonyl), 172.18, 142.85, 140.04, 128.48, 127.44, 125.73, 70.14 (C—OH), 34.58, 32.07, 17.49. IR (neat): 3420 (br, OH), 1690,1639 (C=C—C=O) cm$^{-1}$.

Example 3

Preparation of 3-methyl-2-[phenyl-(2-tetrahydropyranyloxo)-methyl]-2-cyclopenten-1-one 0.440 g (2.17 mmol) of the 2-(hydroxy-phenyl-methyl)-3-methyl-2-cyclopentene-1-one prepared in Example 2 was dissolved in 9.0 mL of methylene chloride. After adding 0.456 g (5.43mmol) of dihydropyran at 20° C., 4.13 mg (0.0217 mmol) of p-toluenesulfonic acid monohydrate was added. Then, the solution was stirred for 2 hours. The obtained reaction mixture was diluted by adding 30 mL of ethyl acetate, and then washed with 5 mL of saturated sodium bicarbonate solution twice. The solution was separated using a separatory funnel. From the organic layer, remaining moisture was removed with magnesium sulfate, and the solvent was removed in vacuo. The obtained product, which included impurities, was separated with column chromatography eluted with a 3:1 (v/v) mixture solution of ethyl acetate and n-hexane. The yield of the obtained compound was 0.530 g (85%).

Example 4

Preparation of 2,5-dimethyl-6-phenylfulvene 0.530 g (1.85 mmol) of the 3-methyl-2-[phenyl-(2-tetrahydropyranyloxo)-methyl]-2-cyclopenten-1-one prepared in Example 3 was dissolved in 10.0 mL of diethyl ether in a Schlenk flask. Then, 1.48 mL (2.22 mmol) of 1.5M methyllithium was added dropwise at −78° C. The temperature was then increased to room temperature, and the reaction was carried out for 7 hours. 10 mL of distilled water was added to the obtained reaction mixture, and diethyl ether was removed in vacuo. After adding 20 mL of ethyl acetate to the mixture solution, the organic layer was taken using a separatory funnel. After adding 20 mL of 2N hydrochloric acid, the separatory funnel was stirred vigorously for 3 minutes. The aqueous layer was discarded and the organic layer was taken. After adding 20 mL of sodium bicarbonate, the aqueous layer was discarded and the organic layer was taken again. After is removing remaining moisture with magnesium sulfate, the solvent was removed completely in vacuo. The obtained product, which included impurities, was dissolved in 5 mL of tetrahydrofuran. Then, 46 mg (2.0 mmol) of NaH and 0.5 mL of methanol were added. After the solution turned red, reaction was carried out at room temperature for 3 hours. Then, the reaction mixture was added to a separatory funnel containing 40 mL each of water and n-hexane. After taking the organic layer, remaining moisture was removed with magnesium sulfate, and the solvent was removed using a vacuum distiller. The obtained product, which included impurities, was separated with column chromatography using a 10:1 (v/v) mixture solution of ethyl acetate and n-hexane. The yield of the obtained compound was 0.200 g (63%).

$^1$H NMR(CDCl$_3$): δ 7.37–7.33 (m, 5H, ph-H), 7.29 (s, 1H, ph-CH), 6.08 (dq, J=3.3, 1.7 Hz, 1H, CH$_3$—C=CH), 6.01 (dq, J=3.3, 1.7 Hz, 1H, CH$_3$—C=CH), 2.10 (s, 3H, CH$_3$), 1.71 (s, 3H, CH$_3$). $^{13}$C NMR (CDCl$_3$): δ 146.33, 136.67, 134.55, 133.52, 132.05, 130.01, 129.32, 129.03, 127.86, 126.97, 16.55 (CH$_3$), 12.66 (CH$_3$).

Differently from the conventional preparation method of fulvene compound through a reaction of a cyclopentadienyl anion or cyclopentadiene with an electrophile, the present invention provides new preparation method of fulvene compound which comprises converting an α-bromoketone having a substituted group at the β-position into a lithium salt of a ketal derivative, followed by transformation into a fulvene by reacting it with an aldehyde or a ketone.

Example 5

Preparation of benzylidene(fluorenyl)(1,3-dimethylcyclopentadienyl)zirconium dichloride 1) 2-[α-Fluorenylbenzyl]-1,3-dimethylcyclopentadiene 0.097 g (0.600 mmol) of fluorene was dissolved in 3.0 mL of tetrahydrofuran. After adding 0.24 mL (2.5M in hexane, 0.600 mmol) of n-butyllithium dropwise at −30° C., the reaction was carried out for 1 hour. 0.110 g (0.600 mmol) of the fulvene compound prepared in Example 4 was added at −30° C., and the solution was reacted at room temperature for about 2 hours. The reaction solution was poured into a separatory funnel containing 4 mL of saturated ammonium chloride solution, and the organic layer was taken with diethyl ether. The remaining moisture was removed from the obtained organic layer with magnesium sulfate, and the solvent was removed in vacuo. The obtained product was separated from impurities with column chromatography eluted with a 10:1 (v/v) mixture solution of n-hexane and toluene. The yield of the obtained compound was 0.160 g (76%).

$^1$H NMR (C$_6$D$_6$): δ 7.65(d, J=7.4 Hz, 2H), 7.4–7.0 (m, 9H), 6.94–6.89 (m, 2H), 5.81 (sextet, 1H, J=1.8 Hz, vinyl-H), 4.83(d, J=11.2 Hz, 1H, Ph-CH or Ph-CHCH), 3.91 (d, J=11.2 Hz, 1H, Ph-CH or Ph-CHCH), 2.60 (quintet, J=1.8 Hz, 2H, CH$_2$), 1.86 (q, J=1.8 Hz, 3H, CH$_3$), 1.63(s, 3H). $^{13}$C NMR (C$_6$D$_6$): δ 147.22, 146.67, 144.49, 143.38, 142.41, 141.60, 138.97, 137.88, 129.98, 129.33, 127.47, 126.86, 126.73, 126.66, 126.62, 126.44, 125.76, 119.96, 119.83, 49.01, 40.79, 44.42, 16.73, 14.92.

2) Benzylidene(1,3-dimethylcyclopentadienyl)(fluorenyl)zirconium dichloride 0.108 g (0.310 mmol) of the 2-[α-fluorenylbenzyl]-1,3-dimethylcyclopentadiene prepared in 1) was dissolved in 3.0 mL of tetrahydrofuran. After adding 0.25 mL (2.5 M in hexane, 0.620 mmol) of n-butyllithium dropwise at −30° C., the solution was stirred for 12 hours. After removing the solvent from the obtained mixture solution in vacuo, it was washed with 4.0 mL of n-pentane and 4.0 mL of benzene. 0.072 mg (0.31 mmol) of zirconium tetrachloride was reacted with the red lithium salt obtained above for 12 hours in 8.0 mL of n-pentane solvent. After the reaction was completed, the solvent was removed from the obtained mixture solution. Then, the solution was extracted with benzene to obtain 12 g (yield: 76%) of metallocene compound. FIG. 1 shows an X-ray diffraction crystal structure of the obtained metallocene compound.

$^1$H NMR (CD$_2$Cl$_2$): δ 8.1–6.9(m, 13H), 6.80 (s, 1H), 6.28–6.19(dd, 2H), 2.21 (s, 3H), 1.82(s, 3H). $^{13}$C-NMR (CD$_2$Cl$_2$): δ 137.67, 128.43, 127.96, 127.75, 127.56, 127.10, 126.45, 126.28, 126.20, 124.94, 124.65, 124.41, 124.24, 124.19, 123.52, 123.41, 123.19, 122.81, 122.34, 121.22, 98.82, 73.59, 41.25, 18.80,16.34.

Example 6

Polymerization of Ethylene 200 mL of toluene solution was put in a high-pressure reactor. Then, 1.8 mL of methylaluminoxane (toluene solution 6.9 wt % Al, density=0.88 g/ml, Akzo) was added to the reactor. The reactor was put into a 70° C. constant-temperature bath and let alone for 30 minutes, so that the temperature of the reactor became identical to that of the bath. 2 mL of the catalyst (concentration=1 μM, toluene solution) prepared in Example 5 was added to the reactor. While applying ethylene at a pressure of 4 atm, the reactor was stirred at 200 rpm. 20 minutes later, the obtained white solid compound was filtered. The solvent was discarded and the filtrate was stirred overnight at room temperature after adding acetone. The solution was filtered to obtain a white solid polymer. Then, it was dried under reduced pressure to obtain 8.5 g of polyethylene polymer.

Example 7

Copolymerization of ethylene and norbornene

Norbornene was dissolved in toluene to make a 56 wt % solution. 200 mL of this solution was put in a high-pressure reactor. Then, 1.8 mL of methylaluminoxane (toluene solution 6.9 wt % Al, density=0.88 c/ml, Akzo) was added to the reactor. The reactor was put in a 70° C. constant-temperature bath and let alone for 30 minutes, so that the temperature of the reactor became identical to that of the bath. 2 mL of the catalyst (concentration=1 µM, toluene solution) prepared in Example 5 was added to the reactor. While applying ethylene at a pressure of 4 atm, the reactor was stirred at 200 rpm. 20 minutes later, the solution was diluted in 600 mL of toluene, and was again diluted with acetone to obtain a white solid compound. The solvent was removed by filtration, and acetone was again added. After stirring at room temperature for 30 minutes, the solution was filtered to give a white solid polymer. Then, it was dried under reduced pressure to obtain 23.0 g of copolymer. The $T_g$ value determined by DSC was 170° C.

Example 8

The same procedure as in Example 7 was carried out, with the pressure changed to 30 psi. 8.5 g of copolymer was obtained. The $T_g$ value determined by DSC was 182° C.

Example 9

The same procedure as in Example 7 was carried out, with the pressure changed to 100 psi. 32.9 g of copolymer was obtained. The $T_g$ value determined by DSC was 149° C.

Example 10

The same procedure as in Example 7 was carried out, with the catalyst amount changed to 4 mL. 41.2 g of copolymer was obtained. The $T_g$ value determined by DSC was 174° C.

Example 11

The same procedure as in Example 7 was carried out, with the reaction temperature changed to 30° C. 11.5 g of copolymer was obtained. The $T_g$ value determined by DSC was 157° C.

Example 12

The same procedure as in Example 7 was carried out, with the norbornene concentration changed to 80%. 34.5 g of copolymer was obtained. The $T_g$ value determined by DSC was 202° C.

Example 13

The same procedure as in Example 7 was carried out, with the norbornene solution changed to a 30% solution. 16.5 g of copolymer was obtained. The $T_g$ value determined by DSC was 162° C.

Comparative Example 1

The same procedure as in Example 7 was carried out, using isopropylene (9-fluorenyl)-cyclopentadienylzirconium dichloride, which is commercially available from Boulder, as the polymerization catalyst. 12.8 g of copolymer was obtained. The $T_g$ value determined by DSC was 170° C.

Comparative Example 2

The same procedure as in Comparative Example 1 was carried out, with the reaction pressure changed to 30 psi. 6.9 g of copolymer was obtained. The $T_g$ value determined by DSC was 177° C.

Comparative Example 3

The same procedure as in Comparative Example 1 was carried out, with the catalyst amount increased to 4 mL. 22.4 g of copolymer was obtained. The $T_g$ value determined by DSC was 173° C.

Example 14

Preparation of 2-(hydroxymethyl)-3-methyl-2-cyclopenten-1-one

The ketal-substituted compound of 2-bromo-3-methyl-2-cyclopenten-1-one (10.3 g, 47.5 mmol) prepared in Example 1 was put in a Schlenk flask containing a tetrahydrofuran solution (120 mL). While keeping the temperature of the flask at −78° C., n-butyllithium (13.17 g, 47.5 mmol) was added dropwise, and the reaction mixture was stirred for 1 hour at the same temperature. Formaldehyde obtained by heating a mixture of p-formaldehyde (4.28 g) and p-toluenesulfonic anhydride (2.23 g) was added to the solution, while still maintaining the temperature at −78° C., using a Schlenk line under a condition of 100° C. and reduced pressure. Reaction was carried out for 3 hours. This solution was heated to room temperature and stirred for 10 minutes. Then, water (100 mL) was added, and the tetrahydrofuran solvent was removed. The water layer was put in a separatory funnel, and the target compound was extracted using 100 mL of methylene chloride, four times. From the methylene chloride solution, moisture was removed with magnesium sulfate, and the solvent was removed using a rotary evaporator. 5.57 g of 2-(hydroxymethyl)-3-methyl-2-cyclopenten-1-one was obtained by column chromatography (hexane:ethyl acetate=1:2) using silica.

$^1$H NMR (CDCl$_3$): δ 4.18 (d, J=4.8 Hz, 2H, OCH$_2$), 3.44 (d, J=4.8 Hz, OH), 2.50–2.42 (m, 2H, CH$_2$), 2.32–2.25 (m, 2H, CH$_2$), 2.04 (s, 3H). $^{13}$C{$^1$H} NMR (CDCl$_3$): δ 209.59 (carbonyl), 173.55 (C=CCO), 138.18 (C=CCO), 54.10 (COH), 34.15 (CH$_2$), 31.75 (CH$_2$), 17.07 (CH$_3$). IR (neat): 3400 (br, OH), 1689 and 1640 (C=C—C=O) cm$^{-1}$. HRMS-El m/z=M$^+$ Calcd. (C$_7$H$_{10}$O$_2$): 126.0678. Found: 126.0681.

Example 15

Preparation of 2-(1-hydroxyethyl)-3-methyl-2-cyclopenten-1-one

The same procedure as in Example 14 was carried out using acetaldehyde instead of formaldehyde. The target compound was obtained by column chromatography (hexane:ethyl acetate=1:1) (yield: 95%).

$^1$H NMR (CDCl$_3$): 64.65 (dq, J=9.6, 6.8 Hz, 1H, OCHCH$_3$), 3.79 (d, J=9.6Hz, 1H, OH ), 2.54–2.52 (m, 2H, CH$_2$ ), 2.41-2.38 (m, 2H, CH$_2$ ), 2.08 (s, 3H, C=C—CH$_3$), 1.41 (d, J=6.8 Hz, 3H, OCHCH$_3$ ). $^{13}$C{$^1$H} NMR (CDCl$_3$):

δ 210.44 (C=O), 170.22, 141.15, 64.47, 34.71, 31.88, 23.47, 17.16. IR (neat): 3420 (br, OH), 1690 and 1640 (C=C—C=O) cm$^{-1}$.

Example 16

Preparation of 3-methyl-2-[(tetrahydropyranyl-2-oxy)methyl]-2-cyclopenten-1-one 2-(hydroxymethyl)-3-methyl-2-cyclopentene-1-one (2.417 g, 19.16 mmol), prepared in example 14, was dissolved in methylene chloride (60 mL). Then, dihydropyran (4.02 g 47.9 mmol) and p-toluenesulfonic acid monohydrate (36 mg, 0.19 mmol) were added at room temperature. This solution was stirred for 2 hours, and then diluted with ethyl acetate (150 mL). The solution was neutralized with a saturated sodium bicarbonate solution (150 mL), and methylene chloride (200 mL) was added for extraction. After taking the organic layer, moisture was removed with magnesium sulfate, and the solvent was removed in vacuo. Pure 3-methyl-2-[(tetrahydropyranyloxy)methyl]-2-cyclopenten-1-one was obtained by column chromatography (hexane: ethyl acetate=1:1) (yield: 94%).

$^1$H NMR (CDCl$_3$): δ 4.64 (t, J=3.4 Hz, 1H, OCHO), 4.36 (d, J=11.2 Hz, 1H, CCH$_2$O), 4.08 (d, J=11.2 Hz, 1H, CCH$_2$O), 3.88 (ddd, J=11.2, 8.0, 3.2 Hz, 1H, OCH$_2$CH$_2$), 3.58–3.46 (m, 1H, OCH$_2$CH$_2$), 2.60–2.50 (m, 2H, CH$_2$), 2.43 (2.35 (m, 2H, CH$_2$), 2.17 (s, 3H, CH$_3$), 1.84 (1.44 (m, 6H) ppm. 13C{1H} NMR (CDCl$_3$): (207.98 (carbonyl), 175.42 (C=CCO), 136.63 (C=CCO), 98.45 (OCHO), 62.09 (CH$_2$O), 57.71 (CH$_2$0), 34.39 (CH$_2$), 32.00 (CH$_2$), 30.45 (CH$_2$), 25.42 (CH$_2$), 19.44 (CH$_2$), 17.63 (CH$_3$) ppm. IR (neat): 1701 and 1650 (C=C—C=O) cm$^{-1}$.

Example 17

Preparation of 3-methyl-2-[(tetrahydropyranyloxy) ethyl]-2-cyclopenten-1-one

The same procedure as in Example 16 was carried out using 2-(1-hydroxyethyl)-3-methyl-2-cyclopenten-1-one (1.53 g, 12.6 mmol) instead of 2-(hydroxymethyl)-3-methyl-2-cyclopenten-1-one to obtain 3-methyl-2-[(tetrahydropyranyloxy)ethyl]-2-cyclopenten-1-one (yield: 93%).

$^1$H NMR (CDCl$_3$): δ 4.80 (q, J=6.8 Hz, 0.5H, OCHCH$_3$), 4.72 (q, J=6.8 Hz, 0.5H, OCHCH$_3$),4.69 (dd, J=2.8, 4.4 Hz, 0.5H, OCHO), 4.41 (dd, J=2.8, 4.4 Hz, 0.5H, OCHO), 3.93–3.87 (m, 0.5H, OCHOCH$_2$), 3.76–3.70 (m, 0.5H, OCHOCH$_2$), 3.51–3.46 (m, 0.5H, OCHOCH$_2$), 3.44–3.39 (m, 0.5H, OCHOCH$_2$), 2.54–2.50 (m, 2H, O=CCH$_2$CH$_2$ or O=CCH$_2$CH$_2$), 2.39–2.36 (m, 2H, O=CCH$_2$CH$_2$ or O=CCH$_2$CH$_2$), 2.26 (s, 1.5H, C=CCH$_3$), 2.20 (s, 1.5H, C=CCH$_3$), 1.89–1.49 (m, 6H), 1.41 (d, J=6.8 Hz, 1.5H, OCHCH$_3$), 1.33 (d, J=6.8 Hz, 1.5H, OCHCH$_3$. $^{13}$C{$^1$H} NMR (CDCl$_3$): δ 207.84 and 207.62 (C=O), 172.75 and 171.81 (O=C—C=C or O=C—C=C), 141.31 and 139.93 (O=C—C=C or O=C—C=C), 97.17, 96.16, 66.77, 65.65, 62.57, 62.40, 34.50, 34.47, 32.24, 32.13, 30.95, 30.78, 25.49, 25.41, 20.51, 19.89, 19.71, 19.28, 17.99, 17.63.

Example 18

Preparation of 1,3-dimethyl-2-[(tetrahydropyranyloxy)methyl]cyclopentadiene compound 3-Methyl-2-[(tetrahydropyranyloxy)methyl]-2-cyclopenten-1-one (4.05 g, 19.2 mmol), prepared in example 16, was dissolved in diethyl ether (50 mL) contained in a Schlenk flask. Then, methyllithium (13.5 mL, 20.2 mmol) was added at –78° C. The reaction mixture was stirred for 3 hours, while heating it to room temperature. After adding water (20 mL), diethyl ether was removed using a rotary evaporator. After adding ethyl acetate (150 mL), the organic layer was separated from the water layer using a separatory funnel. 2N HCl (50 mL) was added to the organic layer. Then, the separatory funnel was stirred for 3 minutes. The water layer was discarded, and the organic layer was neutralized with a saturated sodium bicarbonate solution (40 mL). After collecting the organic layer, moisture was removed with magnesium sulfate, and the solvent was removed using a rotary evaporator.

A pure 1,3-dimethyl-2-[(tetrahydropyranyl-2-oxy)methyl]cyclopentadiene compound was obtained by column chromatography (hexane:ethyl acetate=10:1) using silica (yield: 76%).

$^1$H NMR (CDCl$_3$): δ 5.83 (s, 1H, Cp-H) 4.64 (t, J=3.6 Hz, 1H, OCHO), 4.46 (d, J=11.2 Hz, 1H, CCH$_2$O), 4.20 (d, J=11.2 Hz, 1H, CCH$_2$O), 3.93 (ddd, J=11.2, 8.0, 3.2 Hz, 1H, OCH$_2$CH$_2$), 3.60–3.50 (m, 1H, OCH$_2$CH$_2$), 2.84 (s, 2H, Cp-CH$_2$), 2.04 (s, 3H, CH$_3$), 2.01 (quartet, J=2.0 Hz, 3H, CH$_3$), 1.90–1.50 (m, 6H). $^{13}$C{$^1$H} NMR (CDCl$_3$): δ 143.06 (Cp-C), 142.91 (Cp-C), 136.16 (Cp-C), 123.68 (Cp-CH), 97.62 (OCHO), 62.14 (CH$_2$O), 60.63 (CH$_2$O), 44.37 (Cp-CH$_2$), 30.71 (CH$_2$), 25.61 (CH$_2$), 19.63 (CH$_2$), 14.39 (CH$_3$), 13.87 (CH$_3$). HRMS-EI m/z=M$^+$ Calcd. (C$_{13}$H$_{20}$O$_2$): 208.1460. Found: 208.1463.

Example 19

Preparation of 1,3-dimethyl-2-[1-(tetrahydropyranyloxy)ethyl]cyclopentadiene compound The same procedure as in Example 18 was carried out using 3-methyl-2-[(tetrahydropyranyloxy)ethyl]-2-cyclopenten-1-one instead of 3-methyl-2-[(tetrahydropyranyloxy)methyl]-2-cyclopenten-1-one to obtain a 1,3-dimethyl-2-[1-(tetrahydropyranyl-2-oxy)ethyl]cyclopentadiene compound (yield: 77%).

$^1$H NMR (CDCl$_3$): ( 5.80 (s, 1H, Cp-H) 4.89 and 4.78 (q, J=6.4 Hz, 1H, OCHCH$_3$), 4.80 and 4.41 (dd, J=4.4, 2.4 Hz, 1H, OCHO), 3.93 and 3.45 (dt, J=10.8, 5.6 Hz, 1H, OCH$_2$), 3.71 (ddd, J=12.4, 9.6, 3.2 Hz, 0.5 H, OCH$_2$), 3.44–3.36 (m, 0.5 H, OCH$_2$), 2.81 and 2.78 (quintet, J=2.0 Hz, 2H, Cp-CH$_2$), 2.08 and 2.03 (quartet, J=2.0 Hz, 3H, CH$_3$), 2.02 and 2.00 (s, 3H, CH$_3$), 1.90 ( 1.40 (m, 6H), 1.43 and 1.34 (d, J=6.4 Hz, 1H, OCHCH$_3$). $^{13}$C{1H} NMR (CDCl$_3$): (143.03, 142.83, 141.20, 140.87, 139.36, 137.90, 124.82, 124.46, 95.96, 95.67, 67.76, 66.93, 62.74, 61.64, 44.20, 44.15, 31.04, 30.96, 25.74, 25.67, 21.05, 20.17, 19.82, 19.38, 15.74, 15.56, 14.00, 13.78.

Example 20

Preparation of 2-(indenylmethyl)-1,3-dimethylcyclopentadiene 2-(hydroxymethyl)-3-methyl-2-cyclopenten-1-one (2.98 g, 14.3 mmol) prepared in Example 15 was dissolved in 2 mL of tetrahydrofuran. This solution was added to a solution prepared by stirring indenyllithium (4.36 g, 35.8 mmol) dissolved in 30 mL of tetrahydrofuran at –30° C. The solution was stirred at room temperature for 12 hours. After adding 40 mL of water, the solution was extracted twice with 40 mL of diethyl ether using a separatory funnel. After taking the organic layer, moisture was removed with magnesium sulfate, and the solvent was removed using a rotary evaporator. A pure target compound (2.29 g, yield: 72%) was obtained by column chromatography (hexane:toluene=10:1) using silica.

$^1$H NMR (CDCl$_3$): δ 7.43 (d, J=7.2 Hz, 1H, Ind-H), 7.40 (d, J=7.2 Hz, 1H, Ind-H), 7.30 (td, J=7.2, 0.8 Hz, 1H, Ind-H), 7.19 (td, J=7.2, 0.8 Hz, 1H, Ind-H), 5.93 (quintet, J=2.0 Hz, 1H, Ind-H), 5.86 (d, J=1.6 Hz, 1 H, Cp-H), 3.45 (s, 2H, bridge-CH$_2$), 3.27 (quartet, J=2.0 Hz, 2H, Ind-CH$_2$), 2.87 (s, 2H, Cp-CH$_2$), 1.97 (s, 3H, CH$_3$), 1.84 (quartet, J=2.0 Hz, 3H, CH$_3$). $^{13}$C{$^1$H} NMR (CDCl$_3$): δ 145.27 (Cp-C), 144.47 (Cp-C), 143.81 (Ind-C), 142.44 (Ind-C), 138.51 (Ind-C), 136.95 (Cp-C), 128.52, 125.89, 124.40, 123.57, 123.49, 118.70, 43.99 (Cp-CH$_2$), 37.59 (Ind-CH$_2$), 24.25 (bridge-CH$_2$),14.35 (CH$_3$), 14.05 (CH$_3$).

Example 21

Preparation of 2-(1-cyclopentadienyl)-1,3-dimethylcyclopentadiene

The same procedure as in Example 20 was carried out using 2-(1-hydroxyethyl)-3-methyl-2-cyclopenten-1-one instead of 2-(hydroxymethyl)-3-methyl-2-cyclopenten-1-one and adding cyclopentadienyl sodium instead of indenyllithium to obtain 2-(1-cyclopentadienyl)-1,3-dimethylcyclopentadiene (yield: 64%).

$^1$H NMR (C$_6$D$_6$): δ 6.46–6.02 (m, 3H, Cp-H), 6.80 (s, 1H, Me$_2$Cp-H), 3.78 (quartet, J=7.2 Hz, 0.5 H, bridge-CH$_2$), 3.78–3.68 (m, 0.5 H, bridge-CH$_2$), 3.00 (quintet, J=1.6 Hz, 1H, Me$_2$Cp-CH$_2$), 2.80 (s, 3H, Me$_2$Cp-CH$_2$and Cp-CH$_2$), 1.96 (s, 3H, CH$_3$), 1.84 (quartet, J=2.0 Hz, 1.5 H, CH$_3$), 1.84 (quartet, J=2.0 Hz, 1.5 H, CH$_3$), 1.46 (d, J=7.2 Hz, 1.5 H. CHCH$_3$),1.45 (d, J=7.2 Hz, 1.5 H, CHCH$_3$).

Example 22

Preparation of bis(dimethylamido)[methylene(η$^5$-indenyl)(η$^5$-1,3-dimethylcyclopentadienyl)]zirconium The 2-(indenylmethyl)-1,3-dimethylcyclopentadiene compound (1.72 g, 7.76 mmol) prepared in Example 20 was dissolved in cold diethyl ether (4.0 mL, –30° C.). Then, n-butyllithium (5.29 g, 2.5M, 15.5 mmol) was added to the solution dropwise. After 12 hours of reaction, the solvent was removed under reduced pressure. The remainder was washed with pentane and dried to obtain a dilithium salt compound of 2-(indenylmethyl)-1,3-dimethylcyclopentadiene (1.45 g, yield: 80%).

$^1$H NMR (pyridine-d$_5$): (8.21 (d, J=6.8 Hz, 1H. Ind-H), 8.04 (d, J=6.8 Hz, 1H, Ind-H), 7.22 (d, J=3.2 Hz, 1H, Ind-H), 7.04 (t, J=6.8 Hz, 1H, Ind-H), 7.00 (t, J=6.8 Hz, 1H, Ind-H), 6.71 (d, J=3.2 Hz, 1H, Ind-H), 6.09 (s, 2H, Cp-H), 4.62 (s, 2H, bridge-CH$_2$), 2.45 (s, 6H, CH3). $^{13}$C{$^1$H} NMR (pyridine-d$_5$): (130.04, 128.06, 118.73, 117.57, 117.23, 113.52, 111.10, 110.92, 110.29, 99.87, 92.08, 24.82 (bridge-CH$_2$), 15.12 (CH$_3$).

Figure 2:
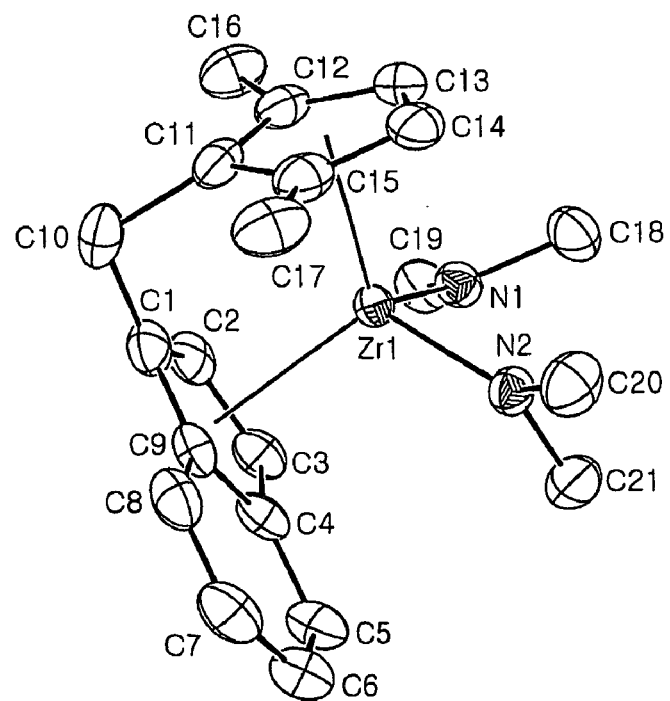
FIG. 2 shows an X-ray diffraction crystal structure of bis(dimethylamido) [methylene($\eta^5$-indenyl)($\eta^5$-1,3-dimethylcyclopentadienyl)]zirconium prepared in Example 22.

The prepared compound (0.5 g, 2.14 mmol) was dissolved in 15 mL of tetrahydrofuran and cooled to –30° C. A ZrCl$_2$(NMe$_2$)$_2$(DME) solution obtained by dissolving 15 mL of tetrahydrofuran therein and cooling to –30° C. was quickly added to the lithium salt and stirred at room temperature for 12 hours. After the solvent was removed, the residue was saturated and recrystallized in pentane at –30° C. to obtain a yellow bis(dimethylamido)[methylene(η$^5$-indenyl)(η$^5$-1,3-dimethylcyclopentadienyl)]zirconium compound crystal (0.44 g) (yield: 52%). FIG. 2 shows an X-ray diffraction crystal structure of the metallocene compound.

$^1$H NMR (C$_6$D$_6$): (7.51 (d, J=8Hz, 1H, Ind-H), 7.45 (d, J=8Hz, 1 H, Ind-H), 6.87 (td, J=8, 0.8 Hz, 1H, Ind-H), 6.72 (td, J=8, 0.8 Hz, 1H, Ind-H), 6.58 (d, J=3.2 Hz, 1H, Ind-H), 5.87 (d, J=3.2 Hz, 1H, Cp-H), 5.85 (d, J=3.2 Hz, 1H, Cp-H), 5.73 (d, J=3.2 Hz, 1H, Ind-H), 3.81 (d, J=14.2 Hz, 1H, bridge-CH$_2$), 3.70 (d, J=14.2 Hz, 1H, bridge-CH$_2$), 2.85 (s, 6H, N(CH$_3$)$_2$), 2.56 (s, 6H, N(CH$_3$)$_2$), 2.13 (s, 3H, CH$_3$), 1.92 (s, 3H, CH$_3$). $^{13}$C{$^1$H} NMR (C$_6$D$_6$): (125.57, 127.32, 125.26, 123.07, 122.34, 121.68, 114.82, 110.56, 107.84, 102.38, 48.65 (N(CH$_3$)$_2$), 47.51 (N(CH$_3$)$_2$), 22.30 (bridge-CH$_2$),14.79 (CH$_3$), 13.75 (CH$_3$).

Example 23

Preparation of [methylene(η$^5$-indenyl)(η$^5$-1,3-dimethylcyclopentadienyl]zirconium dichloride compound The bis(dimethylamido)[methylene(η$^5$indenyl)(η$^5$-1,3-dimethylcyclopentadienyl)]zirconium compound (0.15 g, 0.375 mmol) prepared in Example 22 was dissolved in 1.5 mL of benzene. Then, chlorotrimethylsilane (0.12 g, 1.13 mmol) was added to the solution. After 12 hours of reaction, a yellow [methylene(η$^5$-indenyl)(η$^5$-1,3-dimethylcyclopentadienyl)]zirconium dichloride compound was obtained (yield: 95%).

$^1$H NMR (C$_6$D$_6$): δ 7.26 (dt, J=8.8, 1.2 Hz, 1H, Ind-H), 7.06 (ddd, J=8.8, 6.8, 1.2 Hz, 1H, Ind-H), 7.02 (dt, J=8.8, 0.8 Hz, 1H, Ind-H), 6.74 (ddd, J=8.8, 6.8, 1.2 Hz, 1H, Ind-H), 6.65 (dd, J=3.2, 0.8 Hz, 1H, Ind-H), 6.14 (d, J=3.6 Hz, 1H, Cp-H), 6.11 (d, J=3.6 Hz, 1H, Cp-H), 5.65 (d, J=3.2 Hz, 1H, Ind-H), 3.68 (s, 2H, bridge-CH$_2$), 1.82 (s, 3H, CH$_3$), 1.75 (s, 3 H, CH$_3$). $^{13}$C{$^1$H} NMR (C$_6$D$_6$): δ 126.61, 125.97, 125.62, 124.28, 122.65, 120.56, 113.09, 113.05, 22.13 (bridge-CH$_2$), 14.92 (CH$_3$), 15.70 (CH$_3$). (Carbon with no hydrogen attached was not observed.)

Example 24

Preparation of (bis(diethylamido)ethylidene(cyclopentadienyl)(1,3-dimethylcyclopentadienyl)zirconium The 2-(1-cyclopentadienyl )-1,3-dimethylcyclopentadiene compound (2.17 g, 11.6 mmol) prepared in Example 21 was dissolved in cold diethyl ether (50 mL, –30° C.). After adding methyllithium (14.6 mL, 23.2 mmol), the solution was stirred for 12 hours. The obtained compound was filtered and washed with diethyl ether to obtain a dilithium salt of 2-(1-cyclopentadienyl)-1,3-dimethylcyclopentadiene (yield: 95%).

$^1$H NMR (pyridine-d$_5$): δ 6.29 (s, 4H, Cp-H), 5.96 (s, 2H, Cp-H), 4.63 (quartet, J=7.2 Hz, 1H, CHCH$_3$), 2.40 (s, 6H, CH$_3$), 2.05 (d, J=7.2 Hz, CHCH$_3$). $^{13}$C{$^1$H} NMR (pyridine-d$_5$): δ 131.80, 125.51, 110.33, 102.67, 102.54, 101.37, 33.55 (bridge-CH$_2$), 23.43 (CH$_3$), 16.23 (CH$_3$).

The obtained lithium salt (900 mg, 3.6 mmol) was dissolved in 9 mL of pyridine. Then, ZrCl$_2$(NEt$_2$)$_2$(THF)$_2$ (1.62 g, 3.60 mmol) was added at room temperature. This solution was stirred for 12 hours. The solvent was removed under reduced pressure and the residue was dissolved in pentane and filtered through diatomite. The solution was saturated and let alone at –30° C. for 12 hours to obtain a yellow crystal (920 mg, yield: 49%).

¹H NMR (C₆D₆): δ 6.27–6.22 (m, 1H, Cp-H), 6.16–6.12 (m, 1H, Cp-H), 5.87 (d, J=3.6 Hz, 1H, Me₂Cp-H), 5.84 (d, J=3.6 Hz, 1H, Me₂Cp-H), 5.54 (dd, J=4.8, 2.4 Hz, 1H, Cp-H), 5.33 (dd, J=4.8, 2.4 Hz, 1 H, Cp-H), 3.93 (quartet, J=7.2 Hz, 1H, CHCH₃), 3.41–3.29 (m, 4H, NCH₂), 3.27–3.14 (m, 4H, NCH₂), 2.09 (s, 3H, CH₃), 1.92 (s, 3H, CH₃), 1.63 (d, J=7.2 Hz, 1H, CHCH₃), 1.02 (t, J=6.8 Hz, 3H, CH₃), 1.01 (t, J=6.8 Hz, 3H, CH₃). ¹³C{¹H} NMR (C₆D₆): 125.14 (Cp-C), 123.49 (Cp-C), 116.91 (Cp-C), 115.03 (Cp-C), 113.44 (Cp-CH), 113.04 (Cp-CH), 111.49 (Cp-CH), 111.24 (Cp-CH), 103.50 (Cp-CH), 101.22 (Cp-CH), 47.19 (NCH₂CH₃), 47.03 (NCH₂CH₃), 33.02 (bridge-C), 17.30 (CH₃), 16.83 (CH₃), 14.72 (NCH₂CH₃), 14.49 (NCH₂CH₃), 14.15 (CH₃).

Example 25

Preparation of bis(diethylamido)ethylidene(cyclopentadienyl)(1,3-dimethylcyclopentadienyl)titanium The same procedure as in Example 24 was carried out, using Ti(NMe₂)₂Cl₂ instead of Zr(NMe₂)₂Cl₂.

¹H NMR (pyridine-d₅): δ 6.44 (quartet, 2.0 Hz, 1H, Cp-H), 6.37 (quartet, 2.0 Hz, 1H, Cp-H), 6.18 (d, J=3.2 Hz, 1H, Me₂Cp-H), 6.12 (d, J=3.2 Hz, 1H, Me₂Cp-H), 5.48 (quartet, 2.0 Hz, 1H, Cp-H), 5.17 (quartet, 2.0 Hz, 1H, Cp-H), 3.86 (quartet, J=7.2 Hz, 1H, CHCH₃),2.98 (s, 6H, NCH₃), 2.97 (s, 6H, NCH₃), 2.07 (s, 3H, CH₃),1.95 (s, 3H, CH₃),1.61 (d, J=7.2 H, 3H, CHCH₃).

Example 26

Figure 3:
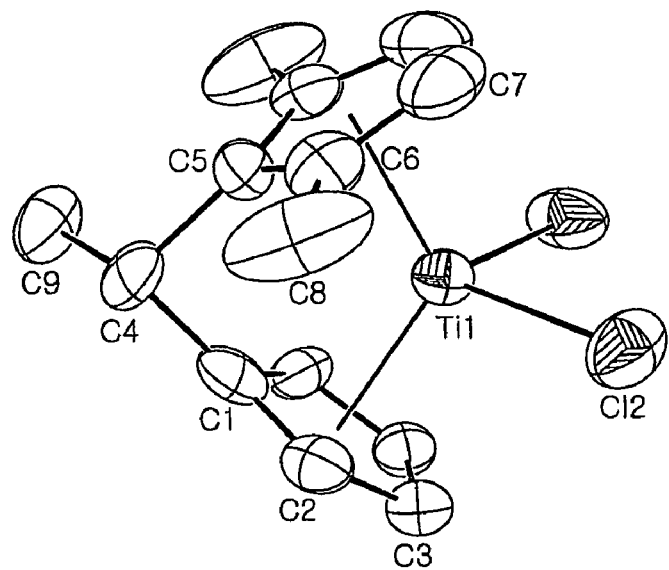
FIG. 3 shows an X-ray diffraction crystal structure of ethylidene (cyclopentadienyl)(1,3-dimethylcyclopentadienyl)zirconium dichloride prepared in Example 26.

Preparation of ethylidene(cyclopentadienyl)(1,3-dimethylcyclopentadienyl)zirconium dichloride The bis(diethylamido)ethylidene(cyclopentadienyl)(1,3-dimethylcyclopentadienyl)zirconium compound (920 mg, 22.2 mmol) prepared in Example 24 was dissolved in 9 mL of benzene. Then, Me₃SiCl (0.846 mL, 66.6 mmol) was added. This solution was stirred for 12 hours to obtain a bright yellow precipitate. After removing the solvent under reduced pressure, the precipitate was dissolved in benzene and filtered through celite. Then, the solvent was removed under reduced pressure to obtain a yellow crystal (730 mg) (yield: 95%). FIG. 3 shows an X-ray diffraction crystal structure of the metallocene compound.

¹H and ¹³C NMR spectra (730 mg, 95%). ¹H NMR (C₆D₆): δ 6.45–6.40 (m, 1H, Cp-H), 6.35–6.33 (m, 1H, Cp-H), 6.19 (d, J=3.6 Hz, 1H, Me₂Cp-H), 6.16 (d, J=3.6 Hz, 1H, Me₂Cp-H), 5.33 (dd, J=4.2, 2.8 Hz, 1H, Cp-H), 5.12 (dd, J=4.2, 2.8 Hz, 1H, Cp-H), 3.70 (quartet, J 7.2 Hz, 1H, CHCH₃), 1.83 (s, 3H, CH₃), 1.66 (s, 3H, CH₃), 1.27 (d, J 7.2 Hz, 1H, CHCH₃) ppm. ¹³C{¹H} NMR (C₆D₆): 124.39 (Cp-CH), 123.31 (Cp-CH), 122.64 (Cp-CH), 121.70 (Cp-CH), 121.15 (Cp-CC), 119.43 (Cp-CC), 118.48 (Cp-CC), 109.17 (Cp-CC), 107.47 (Cp-CH), 105.19 (Cp-CH), 33.12 (bridge-C), 17.41 (CH₃), 16.39 (CH₃), 14.78 (CH₃).

Example 27

Figure 4:
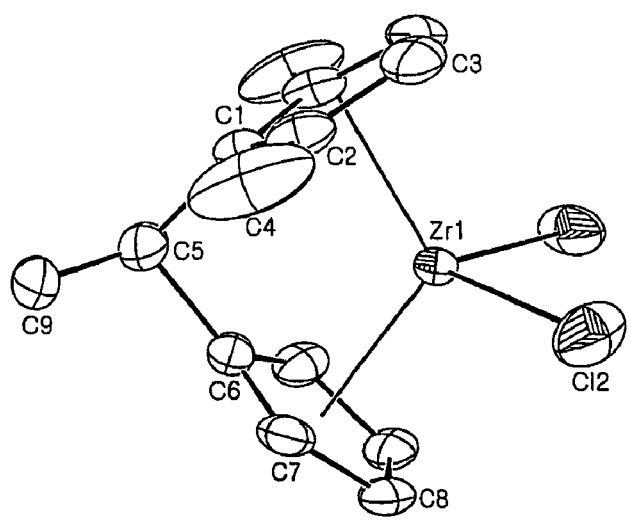
FIG. 4 shows an X-ray diffraction crystal structure of ethylidene (cyclopentadienyl)(1,3-dimethylcyclopentadienyl)titanium dichloride prepared in Example 27.

Preparation of ethylidene(cyclopentadienyl)(1,3-dimethylcyclopentadienyl)titanium dichloride The procedure of Example 26 was carried out using bis(diethylamido) ethylidene(cyclopentadienyl)(1,3-dimethylcyclopentadienyl)titanium prepared in Example 25 instead of bis(diethylamido)ethylidene(cyclopentadienyl)(1,3-dimethylcyclopentadienyl)zirconium. FIG. 4 shows an X-ray diffraction crystal structure of the metallocene compound.

¹H NMR (C₆D₆: pyridine-d₅(10:1)): δ 6.76 (quartet, J=3Hz, 1H, Cp-H), 6.83 (quartet, J=3Hz, 1H, Cp-H), 6.67 (d, J=3.6 Hz, 1H, Me₂Cp-H), 6.64 (d, J=3.6 Hz, 1H, Me₂Cp-H), 5.45 (dd, J=3.6, 2.8 Hz, 1H, Cp-H), 5.18 (dd, J=3.6, 2.8 Hz, 1H, Cp-H), 3.90 (quartet, J 7.2 Hz, 1H, CHCH₃), 1.83 (s, 3H, CH₃), 1.67 (s, 3H, CH₃), 1.40 (d, J=7.2 Hz, 1H, CHCH₃).

Example 28

Copolymerization of ethylene and norbornene

A 70 mL glass reactor containing 70 mL of 3.54M norbonene toluene solution was kept at 60° C. An activated catalyst obtained by mixing 0.5 μmol of [methylene(η⁵-indenyl)(η⁵-1,3-dimethylcyclopentadienyl)]zirconium dichloride and 2 mmol of MAO and stirring them for 15 minutes was added using a syringe. Just after adding the catalyst, polymerization was carried out for 20 minutes while applying an ethylene gas at 100 psig. After the polymerization was completed, the polymerization solution was diluted with acetone. The obtained polymer was filtered and washed several times with acetone. The remaining solvent was removed under reduced pressure to obtain the polymer. The glass transition temperature and molecular weight of the obtained polymer are shown in Table 1.

Example 29

Preparation of 2-[(t-butylamido)phenylmethyl -1,3-dimethylcyclopentadiene compound The 2,5-dimethyl-6-phenylfulvene compound 0.95 g (5.21 mmol) prepared in Example 4 was dissolved in 40 mL of tetrahydrofuran. After cooling to −30° C., 0.41 g (5.21 mmol) of lithium t-butylamide was added. The reaction was carried out for 12 hours while heating to room temperature. After adding 20 mL of water, 50 mL of hexane was added to extract the organic layer. The obtained organic layer was dried using a rotary evaporator. The obtained compound, which included impurities, was purified by column chromatography (hexane:ethyl acetate=1:2) using silica to obtain 1.06 g of pure compound.

¹H NMR (CDCl₃): δ 7.46 (d, J=8Hz, 2H, Ph-H), 7.25 (t, J=8Hz, 2 H, Ph-H), 7.14 (t, J=8Hz, 1H, Ph-H), 5.78 (d, J=2.0 Hz, 1H, Cp-CH), 4.98 (s, 1H, bridge-CH), 2.80 (quintet, J=2.0 Hz, 2H, CH₂), 2.14 (s, 3H, CH₃), 1.82 (quartet, J=2.0 Hz, 3H, CH₃), 1.13 (s, 9H, $^t$Bu-H). ¹³C{¹H} NMR (CDCl₃): δ 145.66 (ph-C$^{ipso}$), 143.11 (Cp-C(CH₃)),143.02 (Cp-C(CH₃)), 137.05 (Cp-C$^{bridge\ head}$), 127.63 (Ph-C), 127.07 (Ph-C), 125.69 (Ph-C), 125.09 (Cp-CH), 52.98 (NCH), 51.41 (NC(CH₃)₃), 44.12 (CH₂), 30.12 (C(CH₃)₃), 15.92 (CH₃), 14.65 (CH₃).

Example 30

Preparation of bis(dimethylamido)[2-(t-butylamido) phenylmethyl]-1,3-dimethylcyclopentadienyl)zirconium compound 0.511 g (2.00 mmol) of the 2-[(t-butylamido)phenylmethyl]-1,3-dimethylcyclopentadiene compound prepared in Example 29 and 0.540 g (2.00 mmol) of Zr(NMe$_2$)$_4$ were dissolved in 30 mL of toluene. The solution was stirred at 100° C. for 2 days while slowly flowing nitrogen gas therein. As dimethylamine and toluene disappeared, a pure white solid bis(dimethylamido)[2-(t-butylamido)phenylmethyl]-1,3-dimethylcyclopentadienyl]zirconium compound suitable for $^1$H and $^{13}$C NMR analyses was obtained.

$^1$H NMR (C$_6$D$_6$): δ 7.61 (d, J=7.6 Hz, 2H, Ph-H), 7.25 (t, J=7.6 Hz, 2H, Ph-H), 7.13 (t, J=7.6 Hz, 1H, Ph-H), 5.88 (d, J=2.8 Hz, 1H, Cp-H), 5.85 (s, 1H, bridge-CH), 5.48 (d, J=2.8 Hz, 1H, Cp-H), 3.09 (s, 6H, NCH$_3$), 2.89 (s, 6H, NCH$_3$), 2.19 (s, 3H, CH$_3$), 1.54 (s, 3H, CH$_3$), 1.24 (s, 3H, CH$_3$), 1.24 (s, 9 H, $^t$Bu-H). $^{13}$C{$^1$H} NMR (C$_6$D$_6$): δ 147.10 (Ph-C$^{ipso}$), 128.45 (Ph-C), 127.64 (Ph-C), 126.45 (Ph-C), 125.43 (Cp-C(CH$_3$)), 123.77 (Cp-C(CH$_3$)), 112.60 (Cp-CH), 107.74 (Cp-CH), 105.76 (Cp-C$^{bridge\ head}$), 59.33 (bridge-CH), 56.20 (NC(CH$_3$)$_3$), 47.37 (N(CH$_3$)$_2$), 43.58 (N(CH$_3$)$_2$), 32.24 (C(CH$_3$)$_3$), 14.79 (CH$_3$), 13.52 (CH$_3$). Anal. Calcd. for C$_{22}$H$_{35}$N$_3$Zr: C, 61.1; H, 8.15; N, 9.71. Found: C, 59.7; H, 7.81; N, 9.53.

Example 31

Figure 5:
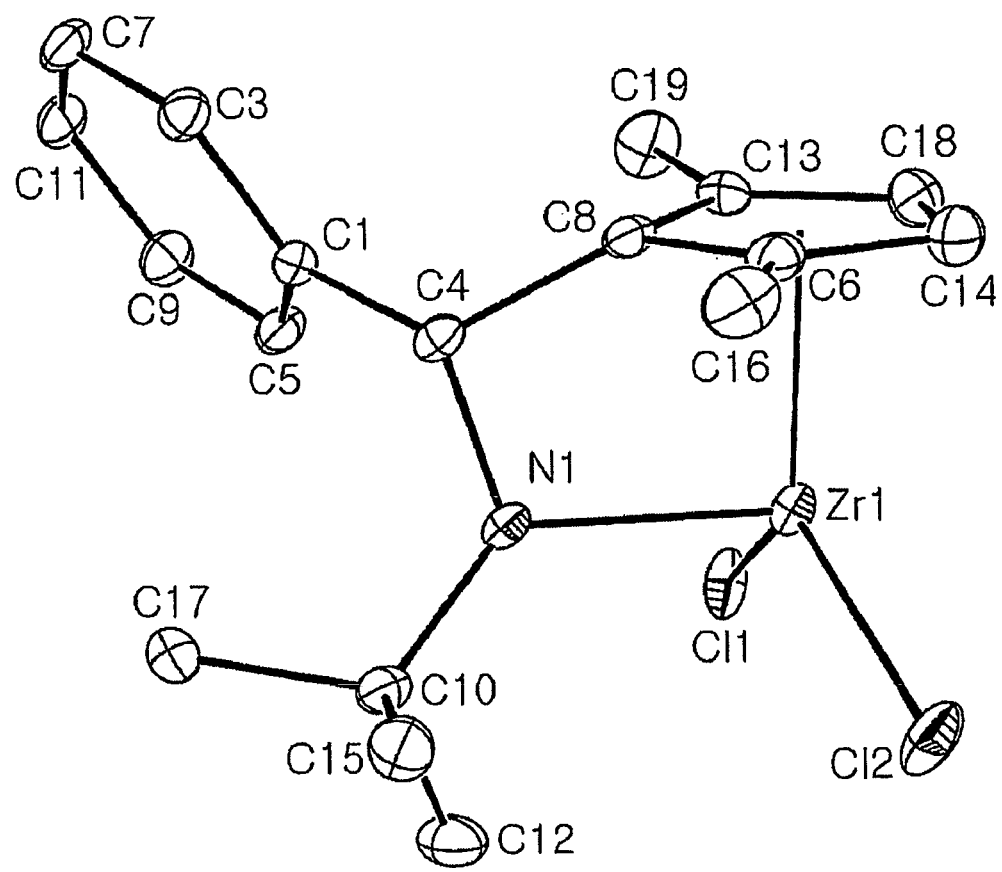
FIG. 5 shows an X-ray diffraction crystal structure of ([2-(t-butylamido)phenylmethyl]-1,3-dimethylcyclopentadienyl)zirconium dichloride prepared in Example 31.

Preparation of [2-(t-butylamido)phenylmethyl]-1,3-dimethylcyclopentadienyl)zirconium dichloride compound 0.530 g (1.22 mmol) of the bis(dimethylamido)[2-(t-butylamido)phenylmethyl]-1,3-dimethylcyclopentadienyl)zirconium dichloride compound prepared in Example 30 was dissolved in 20 mL of toluene. Then, 0.315 g (0.44 mmol) of dichlorodimethylsilane was added. After more than 12 hours of reaction, the produced white solid was filtered off and the solvent was removed under reduced pressure to obtain 0.222 g (yield: 44%) of ([2-(t-butylamido)phenylmethyl]-1,3-dimethylcyclopentadienyl)zirconium dichloride compound. FIG. 5 shows an X-ray diffraction crystal structure of the metallocene compound.

$^1$H NMR (C$_6$D$_6$): δ 7.10–7.22 (m, 2H, Ph-H), 7.10–7.00 (m, 3H, Ph-H), 5.95 (d, J=3.2 Hz, 1H, Cp-H), 5.91 (s, 1H, bridge-CH), 5.77 (d, J=3.2 Hz, 1H, Cp-H), 1.99 (s, 3H, CH$_3$), 1.60 (s, 3H, CH$_3$), 1.27 (s, 9H, $^t$Bu-H). $^{13}$C{$^1$H} NMR (C$_6$D$_6$): δ 142.21 (Ph-C$^{ipso}$), 132.25 (Cp-C(CH$_3$)), 132.17 (Cp-C(CH$_3$), 128.49 (Ph-C), 128.29 (Ph-C), 127.56 (Ph-C), 116.40 (Cp-CH), 116.17 (Cp-CH), 104.27 (Cp-C$^{bridge\ head}$), 59.65 (bridge-CH), 57.84 (NC(CH$_3$), 30.70 (C(CH$_3$)$_3$), 16.58 (CH$_3$), 14.00 (CH$_3$) ppm. Anal. Calcd. for C$_{18}$H$_{23}$Cl$_2$NZr: C, 52.0; H, 5.58; N, 3.37. Found: C, 51.7; H, 6.08; N, 3.34.

Examples 32 to 34

Copolymerization of ethylene and norbornene

Copolymerization was carried out using the same reactor, norbonene solution, and ethylene pressure as in Example 28, changing the catalyst and polymerization condition. The procedure of obtaining polymer after polymerization was the same as in Example 28. The polymerization catalyst used, polymerization condition, and polymerization results are shown Table 1.

TABLE 1

Ethylene/norbonene copolymerization results

| Example | Catalyst* | Time (min) | Temperature (° C.) | Activity (10$^6$ g/mol · h) | T$_g$ (° C.) | M$_w$ | M$_w$/M$_n$ |
|---|---|---|---|---|---|---|---|
| 28 | A | 20 | 60 | 5.0 | 123 | 59900 | 1.73 |
| 32 | B | 5 | 120 | 312 | 129 | 40800 | 1.67 |
| 33 | B | 5 | 90 | 360 | 174 | 54300 | 2.10 |
| 34 | C | 10 | 90 | 5.5 | — | 80500 | 2.04 |

*A: [Methylene(η$^5$-indenyl)(η$^5$-1,3-dimethylcyclopentadienyl)]zirconium dichloride
B: Ethylidene(cyclopentadienyl)(1,3-dimethylcyclopentadienyl)zirconium dichloride
C: Ethylidene(cyclopentadienyl)(1,3-dimethylcyclopentadienyl)titanium dichloride Examples 35 to 38

Copolymerization of ethylene and norbornene

Ethylene polymerization was carried out using the metallocene compounds prepared in Examples 23, 26, and 27, by the method of Example 6. The polymerization catalyst used, polymerization condition, and polymerization results are shown in Table 2.

TABLE 2

Ethylene polymerization result$^a$

| Example | Catalyst | Time (min) | Temperature (° C.)$^b$ | Activity$^c$ | M$_w$ | M$_w$/M$_n$ |
|---|---|---|---|---|---|---|
| 35 | A | 10 | 60 | 43 | 140000 | 1.64 |
| 36 | A | 5 | 60 | 35 | 163000 | 1.70 |
| 37 | B | 8 | 60 | 15 | 235000 | 2.12 |
| 38 | C | 5 | 60 | 57.6 | 246000 | 2.01 |

* A: [Methylene(η$^5$-indenyl)(η$^5$-1,3-dimethylcyclopentadienyl)]zirconium dichloride
B: Ethylidene(cyclopentadienyl)(1,3-dimethylcyclopentadienyl)zirconium dichloride
C: Ethylidene(cyclopentadienyl)(1,3-dimethylcyclopentadienyl)titanium dichloride As can be seen from the above results, a metallocene catalyst having only one bridge carbon at the cyclopentadienyl ligand and a substituent at the α-position to the bridge carbon was prepared from a fulvene derivative having substituents at the 2- and 5-positions. In particular, the metallocene catalysts of Examples 7 to 13, which have a substituent at the α-position of the cyclopentadienyl group only, showed better copolymerization activity and copolymerization ability for cyclic olefins having large steric hindrance like norbornene, than the isopropylene 9-fluorenylcyclopentadienylzirconium dichloride catalyst used in Comparative Examples 2 to 4.

As described above, the novel fulvene compound of the present invention, which has substituents at the 2- and 5-positions, can be used for an intermediate for synthesis of natural product s, for a medicine intermediate, or for a starting material for syntheses of metallocene catalysts having cyclopentadienyl groups.

Also, the bridged metallocene derivative obtained from the fulvene derivative can be used for olefin polymerization, when mixed with an aluminum compound or a boron compound. Since the metallocene catalyst prepared by the present invention has less steric hindrance and offers better electronic effects than the metallocene catalyst prepared by the conventional method, it is useful for copolymerization of large monomers, such as a cyclic olefin copolymer (COC).

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A fulvene compound represented by the following Chemical Formula 7

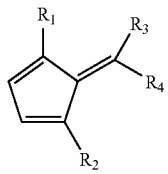

Chemical Formula 7 wherein:

each of $R_1$, and $R_2$ is individually or simultaneously a $C_1$ to $C_{20}$ alkyl, alkenyl, alkylaryl, arylalkyl, or aryl, a $C_1$ to $C_{20}$ alkyl or aryl having an oxygen atom or a nitrogen atom, or a group 14 metalloid radical substituted by a hydrocarbyl; and each of $R_3$ and $R_4$ is individually or simultaneously a hydrogen, a $C_1$ to $C_{20}$ alkyl, alkenyl, alkylaryl, arylalkyl, or aryl, a $C_1$ to $C_{20}$ alkyl or aryl having an oxygen atom or a nitrogen atom, or a group 14 metalloid radical substituted by a hydrocarbyl, and $R_3$ and $R_4$ are linked by an alkylidine radical including an alkyl or aryl radical to form a ring.

2. The compound according to claim 1, wherein both $R_1$ and $R_2$ are methyl radicals.

3. A preparation method of a fulvene compound represented by the following Chemical Formula 7, which comprises:

a) a step of reacting a ketal (dioxolane group) derivative represented by the following Chemical Formula 13 with a metal salt, and reacting it with an electrophile represented by the following Chemical Formula 12, and hydrolyzing it to obtain a compound represented by the following Chemical Formula 11;

b) a step of protecting the alcohol group of the compound represented by Chemical Formula 11 using a compound represented by the following Chemical Formula 10 or by reacting it with dihydropyran or isobutene to obtain a compound represented by the following Chemical Formula 9; and c) a step of nucleophilic reaction of the intermediate compound represented by Chemical Formula 9 with an organometallic compound represented by the following Chemical Formula 8a or Chemical Formula 8b to prepare fulvene compound represented by the following Chemical Formula 7:

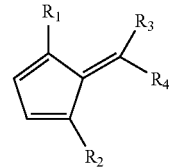

Chemical Formula 7

$R_1$-M  Chemical Formula 8a $R_1$-MgX  Chemical Formula 8b

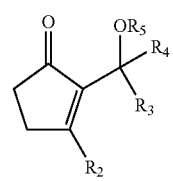

Chemical Formula 9

$R_5$—Y  Chemical Formula 10

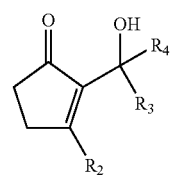

Chemical Formula 11

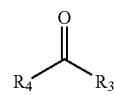

Chemical Formula 12

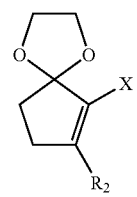

Chemical Formula 13 wherein each of $R_1$, $R_2$, $R_3$, and $R_4$ is independently or simultaneously a hydrogen; a $C_1$ to $C_{20}$ alkyl, alkenyl, alkylaryl, arylalkyl, or aryl; a $C_1$ to $C_{20}$ alkyl or aryl having an oxygen atom or a nitrogen atom; or a group 14 metalloid radical substituted by a hydrocarbyl, wherein at least one of $R_1$ and $R_2$ is not a hydrogen, and $R_3$ and $R_4$ are linked by an alkylidine radical including an alkyl or aryl radical to form a ring;

$R_5$ is a $C_1$ to $C_{20}$ alkyl, alkenyl, alkylaryl, arylalkyl, or aryl; a $C_1$ to $C_{20}$ alkyl or aryl having an oxygen atom or a nitrogen atom; or a group 14 metalloid radical substituted by a hydrocarbyl;

X is a halogen atom;

Y is a leaving group of the nucleophilic substitution, which is a halogen or a sulfonate group including trifluoromethylsulfonate or p-toluenesulfonate; and M is an alkali metal.

4. The preparation method of a fulvene compound according to claim 3, wherein the ketal derivative represented by Chemical Formula 13 is prepared from an unsaturated ketone represented by the following Chemical Formula 14:

Chemical Formula 14

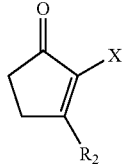

wherein $R_2$ is a hydrogen; a $C_1$ to $C_{20}$ alkyl, alkenyl, alkylaryl, arylalkyl or aryl; a $C_1$ to $C_{20}$ alkyl or aryl having an oxygen atom or a nitrogen atom; or a group 14 metalloid radical substituted by a hydrocarbyl; and X is a halogen atom.

5. A compound represented by the following Chemical Formula 5

Chemical Formula 5

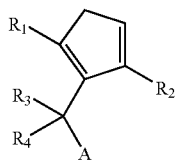

wherein:

each of $R_1$ and $R_2$ is individually or simultaneously a $C_1$ to $C_{20}$ alkyl, alkenyl, alkylaryl, arylalkyl, or aryl, a $C_1$ to $C_{20}$ alkyl or aryl having an oxygen atom or a nitrogen atom, or a group 14 metalloid radical substituted by a hydrocarbyl;

each of $R_3$, and $R_4$ is individually or simultaneously a hydrogen, a $C_1$ to $C_{20}$ alkyl, alkenyl, alkylaryl, arylalkyl, or aryl, a $C_1$ to $C_{20}$ alkyl or aryl having an oxygen atom or a nitrogen atom, or a group 14 metalloid radical substituted by a hydrocarbyl, and $R_3$ and $R_4$ are linked by an alkylidine radical including an alkyl or aryl radical to form a ring; and A is fluorenyl or its derivative, indenyl or its derivative, a substituted or unsubstituted amido, or a substituted or unsubstituted phosphino.

6. The compound according to claim 5, wherein both $R_1$ and $R_2$ of the compound represented by Chemical Formula 5 are methyls; and A is indenyl, fluorenyl, or derivatives thereof substituted by one more substituents selected from the group consisting of a $C_1$ to $C_{20}$ alkyl, alkenyl, alkylaryl, arylalkyl, and aryl.

7. A metallocene compound represented by the following Chemical Formula 1

Chemical Formula 1

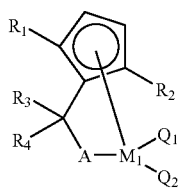

wherein:

each of $R_1$ and $R_2$ is individually or simultaneously $C_1$ to $C_{20}$ alkyl, alkenyl, alkylaryl, arylalkyl, or aryl, a $C_1$ to $C_{20}$ alkyl or aryl having an oxygen atom or a nitrogen atom, or a group 14 metalloid radical substituted by a hydrocarbyl;

each of $R_3$ and $R_4$ is individually or simultaneously a hydrogen, a $C_1$ to $C_{20}$ alkyl, alkenyl, alkylaryl, arylalkyl, or aryl, a $C_1$ to $C_{20}$ alkyl or aryl having an oxygen atom or a nitrogen atom, or a group 14 metalloid radical substituted by a hydrocarbyl, and $R_3$ and $R_4$ are linked by an alkylidine radical including an alkyl or aryl radical to form a ring;

$M_1$ is a group 4 transition metal;

A is fluorenyl or its derivative, indenyl or its derivative, a substituted or unsubstituted amido, or a substituted or unsubstituted phosphino; and each of $Q_1$ and $Q_2$ is individually or simultaneously a halogen; a $C_1$ to $C_{20}$ alkyl, alkenyl, alkylaryl, arylalkyl, or aryl; a $C_1$ to $C_{20}$ substituted or unsubstituted alkylidene; a substituted or unsubstituted amido; or a $C_1$ to $C_{20}$ alkylalkoxy or arylalkoxy, or $Q_1$ and $Q_2$ are linked by an alkylidine radical including an alkyl or aryl radical to form a ring.

8. The metallocene compound according to claim 7, wherein both $R_1$ and $R_2$ are methyls; and A is, indenyl, fluorenyl, or a kind of derivative thereof substituted by one more substituents selected from the group consisting of $C_1$ to $C_{20}$ alkyls, alkenyls, alkylaryls, arylalkyls, and aryls.

9. The metallocene compound according to claim 7, wherein A is a substituted or unsubstituted amido; and all of $R_1$, $R_2$, $R_3$, and $R_4$ are simultaneously $C_1$ to $C_{20}$ alkyls or aryls.

10. A preparation method of the metallocene compound represented by the following Chemical Formula 1, which comprises a step of reacting a fulvene compound represented by the following Chemical Formula 7 with a cyclopentadiene derivative to obtain a compound represented by the following Chemical Formula 5:

Chemical Formula 1

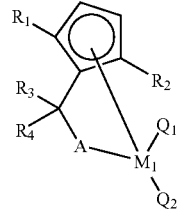

Chemical Formula 5

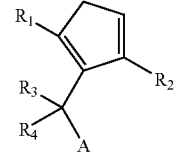

Chemical Formula 7

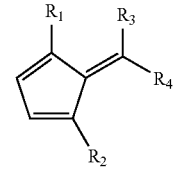

wherein each of $R_1$, $R_2$, $R_3$, and $R_4$ is individually or simultaneously a hydrogen; a $C_1$ to $C_{20}$ alkyl, alkenyl, alkylaryl, arylalkyl, or aryl; a $C_1$ to $C_{20}$ alkyl or aryl having an oxygen atom or a nitrogen atom; or a group 14 metalloid radical substituted by a hydrocarbyl, wherein at least one of $R_1$ and $R_2$ is not a hydrogen, and $R_3$ and $R_4$ are linked by an alkylidine radical including an alkyl or aryl radical to form a ring;

$M_1$ is a group 4 transition metal;

A is cyclopentadienyl or its derivative; fluorenyl or its derivative; indenyl or its derivative; a substituted or unsubstituted amido; or a substituted or unsubstituted phosphino; and each of $Q_1$ and $Q_2$ is individually or simultaneously a halogen; a $C_1$ to $C_{20}$ alkyl, alkenyl, alkylaryl, arylalkyl, or aryl; a $C_1$ to $C_{20}$ substituted or unsubstituted alkylidene; a substituted or unsubstituted amido; or a $C_1$ to $C_{20}$ alkylalkoxy or arylalkoxy, or $Q_1$ and $Q_2$ are linked by an alkylidine radical including an alkyl or aryl radical to form a ring.

11. The preparation method according to claim 10, wherein both $R_1$ and $R_2$ are methyls; and A is cyclopentadienyl, indenyl, fluorenyl, or derivatives thereof substituted by one or more substituents selected from the group consisting of a $C_1$ to $C_{20}$ alkyl, alkenyl, alkylaryl, arylalkyl, or aryl.

12. A preparation method of an ethylenic polyolefin polymer, which comprises a step of polymerizing a monomer selected from a group consisting of ethylene, an α-olefin, a dienic monomer, a trienic monomer, and a styrene monomer in the presence of a metallocene catalyst represented by the following Chemical Formula 1 and a cocatalyst selected from a group consisting of a linear, cyclic, or clustered compound represented by the following Chemical Formula 2, a compound represented by the following Chemical Formula 3, and a compound represented by the following Chemical Formula 4a or Chemical Formula 4b, Chemical Formula 1

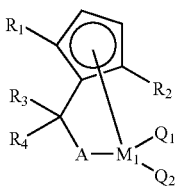

wherein:

each of $R_1$ and $R_2$ is individually or simultaneously a $C_1$ to $C_{20}$ alkyl, alkenyl, alkylaiyl, arylalkyl, or aryl, a $C_1$ to $C_{20}$ alkyl or aryl having an oxygen atom or a nitrogen atom, or a group 14 metalloid radical substituted by a hydrocarbyl;

each of $R_3$ and $R_4$ is individually or simultaneously a hydrogen, a $C_1$ to $C_{20}$ alkyl, alkenyl, alkylaryl, arylalkyl, or aryl, a $C_1$ $C_{20}$ alkyl or aryl having an oxygen atom or a nitrogen atom, or a group 14 metalloid radical substituted by a hydrocarbyl, and $R_3$ and $R_4$ are linked by an alkylidine radical including an alkyl or aryl radical to form a ring;

$M_1$ is a group 4 transition metal;

A is fluorenyl or its derivative, indenyl or its derivative, a substituted or unsubstituted amido, or a substituted or unsubstituted phosphino; and each of $Q_1$ and $Q_2$ is independently or simultaneously a halogen, a $C_1$ to $C_{20}$ alkyl, alkenyl, alkylaryl, arylalkyl, or aryl, a $C_1$ to $C_{20}$ substituted or unsubstituted alkylidene, a substituted or unsubstituted amido, or a $C_1$ to $C_{20}$ alkylalkoxy or arylalkoxy, $$-[Al(R_6)-O]_a-$$  Chemical Formula 2 wherein:

$R_6$ is a halogen, a $C_1$ to $C_{20}$ hydrocarbyl radical, or a $C_1$ to $C_{20}$ hydrocarbyl radical substituted by a halogen; and a is an integer of 2 to 5000, $$N(R_6)_3$$  Chemical Formula 3 wherein:

N is a group XIII element; and each of three $R_6$'s is independently or simultaneously a halogen, a $C_1$ to $C_{20}$ hydrocarbyl radical, or a $C_1$ to $C_{20}$ hydrocarbyl radical substituted by a halogen, and $$[L-H]^{+[NE}{}_4]^-$$  Chemical Formula 4a $$[L]^{+[NE}{}_4]^-$$  Chemical Formula 4b wherein:

L is a neutral or cationic Lewis acid;

N is a group 13 element; and each of four E's is independently or simultaneously a $C_6$ to $C_{20}$ aryl radical substituted by one or more substituents selected from a group consisting of a halogen, a $C_1$ to $C_{20}$ hydrocarbyl, a $C_1$ to $C_{20}$ alkoxy, and a phenoxy radical.

13. The preparation method of a cyclic olefin copolymer (COC) according to claim 12, which comprises a step of polymerizing an α-olefin and a cyclic olefin represented by the following Chemical Formula 15, 16, or 17:

Chemical Formula 15

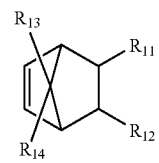

wherein each of $R_{11}$, $R_{12}$, $R_{13}$, and $R_{14}$ is individually or simultaneously a hydrogen; or a $C_1$ to $C_{20}$ alkyl, alkenyl, alkylaryl, arylalkyl, or aryl, wherein $R_{11}$ and $R_{12}$ are linked by an alkylidine radical including an alkyl or aryl radical to form a ring;

Chemical Formula 16

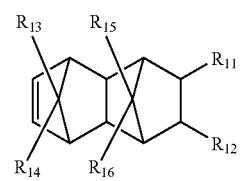

wherein each of $R_{11}$, $R_{12}$, $R_{13}$, $R_{14}$, $R_{15}$, and $R_{16}$ is individually or simultaneously a hydrogen; or a $C_1$ to $C_{20}$ alkyl, alkenyl, alkylaryl, arylalkyl, or aryl, wherein $R_{11}$ and $R_{12}$ are linked by an alkylidine radical including an alkyl or aryl radical to form a ring; and Chemical Formula 17

wherein n is an integer of 2 to 10.

14. The preparation method of a polyolefin polymer according to claim 13, which comprises a step of polymerizing a monomer selected from a group consisting of ethylene, an α-olefin, a dienic monomer, a trienic monomer, and a styrene monomer in the presence of a metallocene catalyst represented by Chemical Formula 1, wherein both $R_1$ and $R_2$ are methyls, and a cocatalyst.

15. The preparation method of a cyclic olefin copolymer (COC) according to claim 13, which comprises a step of polymerizing an α-olefin and a cyclic olefin represented by Chemical Formula 15, 16, or 17 in the presence of a metallocene catalyst represented by Chemical Formula 1, wherein both $R_1$ and $R_2$ are methyls, and a cocatalyst.

16. The preparation method of an α-olefin polymer or a cyclic olefin copolymer (COC) according to claim 12, 13, 14, or 15, wherein the metallocene compound and the cocatalyst are supported on silica or alumina.

* * * * *